United States Patent [19]
Adams et al.

[11] Patent Number: 5,763,400
[45] Date of Patent: Jun. 9, 1998

[54] ECDYSIS-TRIGGERING HORMONE COMPOSITIONS

[75] Inventors: Michael E. Adams, Riverside, Calif.; Dusan Zitnan, Bratislava, Slovakia

[73] Assignee: The Regents of the University of California, Oakland, Calif.

[21] Appl. No.: 582,257

[22] Filed: Jan. 3, 1996

[51] Int. Cl.$^6$ .......................... A61K 38/10; C07K 14/00; C07K 1/14; A01N 63/00
[52] U.S. Cl. .......................... 514/12; 530/412; 530/300; 530/333; 530/344; 530/324; 530/399; 424/405
[58] Field of Search .................................. 530/324, 300, 530/333, 344, 399, 412; 514/12; 424/405; 435/69.4

[56] References Cited

U.S. PATENT DOCUMENTS

| | | | |
|---|---|---|---|
| 3,941,879 | 3/1976 | Okauchi et al. | 514/171 |
| 5,082,828 | 1/1992 | Schooley et al. | 514/12 |

OTHER PUBLICATIONS

Akai, H., "Ultrastructure of Epitracheal Gland during Larval–Pupal Molt of Bombyx mori," *Cytologia*, 57:195–201, 1992.

Hesterlee, Sharon and Morton, David B., "Insect Physiology: The Emerging Story of Ecdysis," *Current Biology*, 6(6):648–650, 1996.

Maeda et al, "Insecticidal Effects of an Insect-Specific Neurotoxin Expressed by a Recombinant Baculovirus," *Virology*, 184:777–780, 1991.

Reagan, Jeff D., "Expression Cloning of an Insect Diuretic Harmone Receptor: A Member of the Calcitonin/Secretin Receptor Family," *Journal of Biological Chemistry*, 289(1):9–12, Jan. 1994.

Tomalski, Michael D. and Miller, Lois K., "Insect Paralysis by Baculovirus–Mediated Expression of a Mite Neurotoxin Gene," *Nature*, 352:82–88, Jul. 1991.

Trimmer, et al, "Purification and Characterization of FMR-Famildelike Immunoreactive Substances From the Lobster Nervous System: Isolation and Sequence Analysis of Two Closely Related Peptides," *Journal of Comparative Neurology*, 266:16–26, 1987.

Truman, James W., "Ecdysis Control Sheds Another Layer," *Science*, 271:40–41, Jan. 1996.

Zitnan, et al, "Identification of Ecdysis–Triggering Hormone From an Epitracheal Endocrine System," *Science*, 271:88–91, Jan. 1996.

Tublitz et al 1992 (J. Exp. Biol. 165,265).

Tublitz et al 1985 (J. Exp. Biol. 114, 381).

*Primary Examiner*—David L. Fitzgerald
*Assistant Examiner*—Michael D. Pak
*Attorney, Agent, or Firm*—Denise L. Mayfield

[57] ABSTRACT

Unique ecdysis triggering hormone nucleic acid molecules and ETH peptides/proteins having biological activity for promoting ecdysis in insects are disclosed. Methods of preparing the peptides/proteins by recombinant means, and use of the peptide/proteins in an insect controlling agent are also provided. Methods of inducing ecdysis using the sequences encoding the ETH peptides/proteins are outlined. Insecticidal preparations that are specific to insects that shed their skin, and that do not pose an environmental threat to humans or animals, are also disclosed employing the nucleic and molecules and peptides and proteins they encode. Processes employing the ETH nucleic acid encoding sequences to identify ETH receptors are also defined. The ETH receptors are employed in screening assays to select organic molecules capable of binding the ETH receptor and inducing ecdysis and eclosion, particularly in insects. Methods of using the ETH nucleic acid molecules in genetic engineering of plants and insects are also disclosed.

18 Claims, 3 Drawing Sheets

ECDYSIS-TRIGGERING HORMONE COMPOSITIONS

This invention was made with Government support under Grant No. NS24472, awarded by the National Institutes of Health and Grant Nos. 92-37302-7470 and 93-37302-8968, awarded by the United States Department of Agriculture. The Government has certain rights in this invention.

BACKGROUND OF THE INVENTION

1. Field of the Invention

The present invention relates to the field of proteins that regulate insect development, and the use of proteins and agents derived therefrom in insect controlling preparations. Recombinant proteins and peptides with insecticidal activity, as well as isolated DNA molecules encoding them, vectors that include nucleic acid sequences encoding the proteins/peptides, and methods of preparing these various preparations of proteins/peptides of ETH are also related to the invention. The invention also relates to insect hormone receptors and uses of such receptors in screening methods for organic molecules that bind receptor for ecdysis triggering hormone or eclosion hormone.

2. Description of the Related Art

Hormones and other peptide-based agents regulate a number of developmentally important processes in a wide range of invertebrate and vertebrate systems. For example, FMRF (SEQ ID NO. 29) amide-related peptides have been reported to exert cardioactivity in mollusc, to effect membrane conductances of mammalian neurons, to modulate the heartbeat of the leech, to affect blood pressure in a rat, and to modulate stomatogastric pyloric rhythm (Trimmer, 1987). The carboxy-terminal sequence -Arg-Phe-amide has been reported to be important for the pharmacological actions of these peptides, and distinguishes this family of peptides from another group of peptides, the pancreatic polypeptide family, that has a C-terminal sequence -Arg-Tyr-amide (Trimmer, 1987). This family of peptides has similarities to the opioid peptide families of vertebrates.

Hormones are also important in the developmentally important process of ecdysis. Ecdysis, or the repeated shedding of old cuticle via a series of highly stereotyped motor movements, is critical to the maturation of insects and crustaceans. The endocrinology and physiology underlying ecdysis has been extensively studied by Truman and colleagues in lepidopteran insects, a group of insects that undergo complete metamorphosis (Truman (1992), Prog. Brain Res. 92:361-74); Truman et al (1993), In: Insect Neurochemistry and Neurophysiology 1993, pp. 39-51. London:CRC Press). Lepidopteran insects pass through several larval stages and a pupal stage prior to reaching the winged, reproductive adult stage.

The shedding of cuticle in Manduca, Bombyx and other lepidopterous insects is characterized by two main patterns of sterotypic motor movements. First is the pre-ecdysis behavior, which serves to separate the underlying new cuticle from the old. In pharate larval and pupal stages of *Bombyx mori*, pre-ecdysis behavior consists of robust synchronous dorso-ventral contractions, which typically lasts for 45-60 minutes. In pharate adults, pre-ecdysis behavior has been observed by the present inventors to involve rotary movements of the abdomen. In Manduca, the pre-ecdysis motor pattern varies considerably with stage, being robust and well-defined in pharate larvae and much weaker in pharate pupae and adults (Copenhaver et al. (1982), J. Insect. Physiol. 28:695-701); Truman et al. (1980), J. Exp. Biol. 88:327-337).

Pre-ecdysis is followed by ecdysis behavior. Ecdysis behavior serves to first rupture the old cuticle along the anterior midline, allowing the insect with its newly formed cuticle to emerge. The anteriorally-directed peristaltic waves characteristic of ecdysis behavior are similar in all developmental stages. These behaviors emerge from the ventral nerve cord as rhythmic patterned bursts of motor output to the body wall musculature.

Ecdysis has been previously reported to be triggered by the release of a neuropeptide hormone, called eclosion hormone (EH). More specifically, in work by others in the moth, eclosion hormone reportedly initiates biochemical and physiological events that culminate in ecdysis; however the precise endocrine signals triggering this process were unclear (Copenhaver and Truman, 1982; Hewes and Truman, 1991; Truman, 1992; Truman, J. W., et al., in: *Insect Neurochemistry and Neurophysiology* 1993; Ewer, 1994).

The efficacy and timing of eclosion hormone action in vitro and in vivo on the nervous system has also been examined. In studies by Truman and others, extracts of corpora cardiaca (CC) as a source of the eclosion hormone, were reportedly capable of triggering premature ecdysis in all life stages., larva, pupa and adult upon injection of the CC extract into the hemocoel (Truman et al. 1978, J. Exp. Biol., 74:151). However, the window of sensitivity to eclosion hormone proved to be quite narrow, some 6-12 hours prior to the natural event. Injections prior to this critical period reportedly had no effect (For review, see Truman, 1978). Hence, sensitivity to this agent is restricted to a relatively small developmental time window.

The use of eclosion hormone for insect control has been described in U.S. Pat. No. 5,082,828. This patent relates to the topical application of eclosion hormone, characterized as a 62 amino acid protein, for disrupting the normal growth and maturation process of insects, resulting in the death of the organism. However, peptide preparations of eclosion hormone suffer the disadvantage of minimal surface activity, peptides being charged molecules that have minimal cuticle penetrating potential.

The gene for eclosion hormone and its corresponding cDNA from *Manduca sexta* has also been described (Horodyski et al. (1993) , P.N.A.S. 86:8123-8126). Nucleotide probes have been prepared from this information and used to confirm the identity of eclosion hormone-producing cell bodies by in situ hybridization (id.). However, the receptor for eclosion hormone has not yet been described.

Despite the availability of the eclosion hormone, and the availability of the gene and corresponding cDNA sequence, the receptor for this hormone has not been described. This may in part be due to teaching in the art that eclosion hormone acts on the nervous system (Truman et al. (1978), J. Exp. Biol. 74: 151), thus leading workers to seek the receptor in nerve tissue. To the present workers knowledge, such attempts have been unsuccessful.

Characterization of an eclosion hormone receptor would provide an avenue for selecting small, organic molecules that bind the receptor, thus providing excellent candidate molecules for formulation as topically active insect regulatory preparations and insecticides.

Because of irreversible changes that occur within the new cuticle during ecdysis, the behavior can only be performed once. Hence, a failure in the coordinated sequence of behaviors during pre-ecdysis and ecdysis results in crippling deformities to the animal, or in the insect being fatally trapped in their old skin-each ecdysis presenting a potential crisis point in an insect's life history.

Manipulation of developmental events during ecdysis, such as with the eclosion hormone described above, have been proposed in several strategies for synchronizing insect development and in insect population control. For example, U.S. Pat. No. 4,910,201 describes pyridazinone derivatives and their uses in insecticidal compositions, these agents reportedly disturbing metamorphosis and ecdysis of insect pests. The inhibition of ecdysis reportedly causes some pests to die and thus, with residual action of the described compounds, the compounds provide control of insect pests.

Controlling insect development, and ecdysis, using biologically active hormones, has been used in several insect-based industries, such as in the silk industry. For example, JP 79042912 and JP 50029371 (both to Ajinomoto KK) relate to cultivation of silkworms by feeding with an ecdysis hormone component and juvenile hormone. JP 51013684 (to Takeda) also employs biologically active hormones in combination with contamination controlling agents, as part of a method for preventing internal silkworm contamination. This method, more specifically, provides for treatment with steroid-like molting hormone (including alpha- and beta-ecdysone, inokosterone, cyasterone and ponasterones A and B), juvenile hormone and antibiotics at specific developmental stages.

These approaches suffer several disadvantages, most significantly a relatively limited effectiveness because of the narrow window of susceptibility of insects to these types of steroid-like hormones. On a commercial scale, such agents for insecticidal applications are relatively ineffective, providing for disruption of insect development only at the end of a molt episode.

Insects, including lepidopteran insects, continue to elicit significant loss to many commercially important agricultural crops, including gains (corn, wheat, cotton, soybeans), and various vegetable, fruit (grapes, apples, peaches), and nut crops (almonds, walnuts). Hence, significant economic incentive exist for developing safer and more economic insect controlling strategies.

Conventional insect pest control methods rely primarily on relatively toxic, and non-specific chemical formulations, and have become increasingly unacceptable because of potential toxicities to humans and animals, as well as destruction of desirable plant and animal life. The continued threat such agents pose to the environment add to the growing need for more bio-compatible, specific, yet effective, insect population control techniques. Repeated use of conventional chemical insecticides also enhances the potential for insect resistance, resulting in increased risk of insecticide resistant insect strains and reduced agent effectiveness.

Improvements are also needed in hormonally-based insect control approaches, such as those described using eclosion hormone and juvenile hormone. Specifically, preparations that are less limited in range of effectiveness against developmentally unsynchronized populations of insects and other molting animals are still lacking. An unsatisfied need continues to exist in the art of insect management and control, despite recent advances in the understanding of the biology of these and related animals.

SUMMARY OF THE INVENTION

The present invention discloses the existence of a new and developmentally important family of peptide hormones that have surprising and unexpectedly broad-reaching developmental bioactivity. These hormones, and their related hormones, are characterized collectively here as the ecdysis triggering hormone (ETH) family of peptides and proteins. The potent biological activity of these proteins and peptides is further described as a capability for disturbing pre-ecdysis and/or ecdysis behavior during essentially all stages of insect development.

In initial studies, ETH was isolated from epitracheal glands (EG) of insects, particularly leptiderigic insects. Elucidation of the amino acid and nucleic acid sequences of these proteins, and the existence of tissues/glands homologous to these epitracheal glands in many other insects and animals, provide a number of different natural sources from which these active agents may be derived. For example, it is expected that bioactive ETH and related peptides may be purified relative to their naturally occurring state from endocrine organs of virtually any animal that undergoes ecdysis.

The ETH, ETH precursor, as well as ETH precursor related peptides 1 and 2, have been isolated in purified form relative to their naturally occurring state and substantially free from other associated insect polypeptides. With the present disclosure of the inventors, the compositions of ETH and its precursor related peptides may now be conveniently obtained from insects, intact insect cells (e.g., Inka cells), cell-free lysates, as well as culture medium from cells that express or excrete these proteins.

The identification of the amino acid sequences of this unique family of proteins, as well as the nucleic acid molecules encoding them, are also described here. Hence, the ETH, ETH-PRP1 and ETH-PRP2 described herein may also be prepared in their synthetic and recombinant forms.

The ETH and the ETH precursor related peptides 1 (ETH-PRP1) and 2 (ETH-PRP2), may be further defined as non-steroidal in nature, an additional characteristic that distinguishes them over previously described ecdysis hormone, such as those employed in silkworm cultivation. The presently claimed ETH- and ETH related proteins/peptides are also specific for insects, ecdysis being an insect specific behavior. The proteins and bioactive peptides thereof are thus particularly compatible for use as insecticides on food and other products intended for livestock or human consumption, as well as for use in urban settings.

As used herein, ETH is understood to include one or more components which may contribute to the ecdysis triggering hormone activity described here. Ecdysis triggering hormone activity is defined as the activity of the peptide, protein, or organic molecule, or biologically active fragment thereof, to trigger the behavioral events leading to the initiation of ecdysis or pre-ecdysis events, the release of these bioactive molecules being further defined as capable of being triggered by eclosion hormone.

In some embodiments, ETH is shown to be functionalized at its carboxy (COOH—) terminus. For example, SEQ ID NO:1 is represented as having a carboxy terminus Pro-Arg-Met-NH$_2$, SEQ ID NO:2 as PRM-NH2, and SEQ ID NO:3 and PRM-NH2. Thus, in some embodiments, the carboxy terminus is amidated. However, other functionalizations are also contemplated as useful in the practice of the present invention. For example, derivatization of the amine to form a secondary or tertiary amine, or substitutions for the amine, such as phosphate, sulfate or carbohydrate.

In some embodiments, a screening method for candidate substances having ETH activity is defined, comprising: exposing a candidate substance to the antibody for ETH, to a lepidopteran pharate pupa or pharate adult and monitoring onset of ecdysis triggering activity relative to onset with eclosion hormone, and to an isolated insect nerve cord preparation absent tracheal tissue and monitering ecdysis motor patterns; and selecting a candidate substance having binding affinity for the antibody, inducing ecdysis in the pharate pupae or pharate adult prior to eclosion hormone, or eliciting ecdysis motor patterns in the isolated insect nerve cord preparation absent a tracheal system, as a candidate substance having ecdysis triggering activity.

A method for preparing ecdysis triggering hormone purified relative to its naturally occurring state is also provided. In one embodiment, the method comprises obtaining epitracheal glands of lepidopteran insects to provide a lepidopteran epitracheal gland preparation; extracting the lepidopteran epitracheal gland preparation in saline to provide an extracted lepidopteran epitracheal gland extract; heating the extract to provide a heat-treated insect extract; cooling the heat-treated extract to provide a cooled insect extract; centrifuging the cooled insect extract; and collecting the supernatant, said supernatant comprising the ecdysis triggering hormone having a molecular weight of between about 2000 to about 3500 Da as determined by liquid secondary ion mass spectrometry, purified relative to its naturally occurring state.

In another embodiment, the method comprises extracting ETH from insects using reversed-phase liquid chromatography (RFLP), and collecting biologically active fractions comprising ecdysis triggering hormone-like activity. However, many other extraction and separation methods known to those of skill in the art may be used to obtain fractions containing the ecdysis triggering hormone or proteins/peptides or other organic molecules having ecdysis triggering hormone-like activity.

The present inventors have also characterized a peptide motif of the ecdysis triggering hormone peptide. In one embodiment, this peptide motif comprises an octapeptide having an amino acid sequence found to comprise part of the ecdysis triggering hormone amino acid sequence found in Manduca and Bombyx. (SEQ ID NO:1).

The ETH has been determined to have a molecular weight of between about 2000 to about 3500 Da as determined by liquid secondary ion mass spectrometry. In other embodiments, the ETH protein may be defined as having a molecular weight of about 2500 Da to about 3000 Da, again as determined by liquid secondary ion mass spectrometry. In even further embodiments, the ETH has a molecular weight that lies in the range of about 2,600 to about 3,000 Da. In *Manduca sexta*, the ETH peptide has a molecular weight of about 2940.45 Da (calculated mass of the free acid is 2941.44 daltons). Synthetic forms of the ETH have a molecular weight of 2940.4±0.1 daltons. In *Bombyx mori*, ETH is slightly smaller, and has been determined to have a slightly lower molecular weight (3 amino acids smaller) of about 2,658 Da, again as determined by liquid secondary ion mass spectrometry. The ETH precursor peptide in one embodiment has a molecular weight of about 5580–5800.

It will be understood by those of skill in the art that the determination of the molecular weight of the ecdysis triggering hormone peptides/proteins may vary in accordance with the particular method used for the determination of molecular weight, as well as between species of insects, within the above ranges.

Provided to an insect prior to the period when ecdysis normally occurs, the ETH and gene related proteins/peptides of the invention act to induce ecdysis of the insect, the insect then becoming trapped permanently in the old cuticle layer. Alternatively, the presence of ETH at inappropriate developmental times will trigger premature ecdysis behavior, rendering the insect unable to respond to its own hormone at the appropriate developmental time. ETH is also effective at inhibiting later stage insects, as application of ETH to adult insects causes premature eclosion of the insect pharate adult stage. These treated adult insects are unable to inflate their wings completely, thus limiting their mobility and reproductive success.

Provided to a mixed population of insects representing diverse developmental stages, ETH and its related proteins/peptides, or biologically active fragments thereof, as well as receptor binding organic molecules, are expected to provide effective, specific and environmentally compatible insecticides, as well as have insect synchronization uses. These characteristics define ETH peptides, proteins, receptor binding agents, and analogs thereof as novel biological insecticides.

The ETH protein or bioactive fragments thereof, may be defined in some embodiments as comprising an amino acid sequence selected from the group consisting of an N-terminal SNEA (SEQ ID NO:26) C-terminal -PRM; and an internal -MGYVIK (SEQ ID NO:27) sequence, the ETH having ecdysis triggering hormone-like activity. In other embodiments, the ETH preparations comprise a peptide having at least an octapeptide sequence, TNKNIPRM (SEQ ID NO:1). In one particular embodiment, an ETH of *Manduca sexta* is provided , in these embodiments the peptide comprising an amino acid sequence as defined in SEQ ID No:3. In these preparations, the peptide is further defined as comprising a 26-mer, and in particular preparations, comprises an amidated carboxy terminus.

The invention also provides nucleic acid molecules of ETH and its related peptides and precursor molecules. In some embodiments, the nucleic molecules of the present invention comprise at least a 20 nucleotide segment of a defined nucleic acid sequences, such as that set forth by reference to SEQ ID NO: (e.g., 16, 17, 18, or 19), the molecule being capable of hybridizing to the nucleic acid sequence designated under hybridization stringency conditions standard for hybridization fidelity and stability. These respective molecules may be further defined as comprising a nucleic acid sequence substantially free of insect or lepidopteran nucleic acid sequences that do not encode the ETH, ETH-precursor, or ETH-precursor related peptide 1 or 2 to which the sequence ID NO: refers.

The cDNA encoding an ecdysis triggering hormone precursor is a further embodiment of the invention, said cDNA having a sequence essentially as set forth in SEQ ID NO:16. Expression vectors that comprise a nucleic acid molecule having a sequence operably linked to a promoter of DNA expression, said sequence selected from the group consisting of SEQ ID NO:16, 17, 18, 19, 20, 21, 22, 23, 24, are also provided. The expression vector in a particular embodiment is defined as pcDM8. Bacterial host cells comprising the aforedescribed expression vectors are also provided.

The isolated DNA molecules of the invention also may be described as a molecule selected from the group consisting of: (a) cDNA encoding a biologically active ETH having a nucleotide sequence derived from the coding region of the sequence at: SEQ ID NO:16; (b) a DNA capable of hybridizing to the cDNA of (a) under moderate conditions of stringency and which encodes biologically active ETH; and (c) a DNA which is degenerate as a result of the genetic code to the DNA defined in (a) or (b) and which encodes biologically active ecdysis triggering hormone.

In other embodiment, an isolated DNA molecule consisting essentially of a nucleotide sequence selected from the group consisting of a nucleotide sequence which encodes an ecdysis triggering hormone, a nucleotide sequence which encodes an antigenic fragment of said ETH, and a nucleotide sequence which hybridizes to the nucleotide sequence encoding said hormone, is provided.

Recombinant host cells and recombinant vectors that incorporate an isolated DNA segment in accordance with the isolated DNA molecule as described above, are also disclosed. A particular recombinant vector that may be used is a pCRII vector.

ETH PRECURSOR

The ETH precursor has also been identified by the present inventors, and is characterized as containing the coding sequences for at least three of the ecdysis triggering hormone peptides, ETH, ETH-PRP1, and ETH-PRP2. These are individually described below, and have been found to have somewhat different and in some instances synergistic, when used in combination. In one particular embodiment, the ETH precursor is further defined as comprising an amino acid sequence as defined in Table 3, from amino acid Met at position 1 to amino acid Arg at position 114. The amino acid sequence of this particular ETH precursor is also provided at SEQ ID NO:15.

The nucleic acid molecule encoding one particular ETH precursor is further defined as being encoded by a nucleic acid sequence comprising the sequence essentially as defined at Table 4, extending from nucleic acid A at position 1 to nucleic acid A at position 345. The nucleic acid sequence of this particular ETH precursor is also provided in the sequence at SEQ ID NO: 16.

ETH

The ecdysis triggering hormone, and ecdysis triggering hormone active fragments thereof, may be generally described as non-steroidal. These peptides/proteins are capable of inducing pre-ecdysis or ecdysis behaviors in an animal at earlier developmental. stages than eclosion hormone. ETH, in particular embodiments, may be further defined as having a molecular mass of between about 2,000 to about 3500 Da, as determined by liquid secondary ion mass spectrometry.

The ecdysis triggering hormone of the invention has been isolated and sequenced from at least two different lepidopteran insects, *Manduca sexta* and *Bombyx mori*. Table 3 depicts the 26-mer ecdysis triggering hormone purified relative to its naturally occurring state from the *Manduca sexta* ETH. This embodiment of ETH may be further defined as comprising an amino acid sequence corresponding to amino acid Ser at position 37 to amino acid Met at position 62 of the ETH precursor molecule illustrated at Table 3. The isolated amino acid sequence of the *Manduca sexta* ETH is also provided at SEQ ID NO:3.

In another embodiment of ETH-related molecules, further nucleic acid molecules encoding the *Manduca sexta* ETH provided. The ETH nucleic acid molecule, in one embodiment, comprises a nucleic acid sequence encoding an ETH having an amino acid sequence essentially as defined in SEQ ID NO:3. In another embodiment, the ETH nucleic acid molecule comprises a nucleic acid sequence essentially as defined from nucleic acid A at position 109 to nucleic acid G at position 186 of the ETH precursor nucleic acid sequence defined in Table 4. The nucleic acid sequence for the *Manduca sexta* ETH is also provided at SEQ ID NO:18.

Another embodiment of ETH from *Bombyx mori* is also provided. In this embodiment, an ETH comprising an amino acid sequence essentially as defined at SEQ ID NO:2 is identified. A nucleic acid molecule encoding the *Bombyx mori* ETH is also disclosed, this nucleic acid molecule comprising a nucleic acid sequence encoding an ETH having an amino acid sequence essentially as set forth in SEQ ID NO:2.

ETH-PRP1

An ETH-PRP1 peptide is also defined as part of the present disclosure. This peptide is identified here to constitute a segment of the ETH precursor identified in *Manduca sexta*, the sequence of ETH-PRP1 being located downstream from the *Manduca sexta* ETH as described above. The ETH-PRP1 peptide comprises a significantly large segment of the ETH precursor identified in Table 3. ETH-PRP-1 has also been characterized having cardioactivity, and as having pre-ecdysis stimulating activity. The ETH-PRP1, in one particular embodiment, has a molecular weight of about 5,500 to about 5,800 Da, as determined by liquid secondary ion mass spectrometry. In one particular embodiment, ETH-PRP1 isolated from Manduca is described, the peptide determined to have a molecular weight of about 56,600 Da, again as determined using the same method. This ETH-PRP1 comprises a 47-mer peptide having an amino acid sequence essentially as defined by the sequence corresponding to amino acid Asn at position 66 through amino acid Met at position 112 of the ETH precursor sequence (See Table 3). This amino acid sequence is also provided at SEQ ID NO:14.

A nucleic acid molecule having a sequence encoding an ETH-PRP1 constitutes still another embodiment of the invention. In one aspect, the ETH-PRP1 nucleic acid molecule comprises a nucleic acid sequence encoding an ETH-PRP1 having an amino acid sequence essentially as defined in SEQ ID NO:14. In even further embodiments, the nucleic acid molecule for ETH-PRP1 is defined as comprising a nucleic acid sequence essentially as defined by the sequence from nucleic acid A at position 196 to nucleic acid A at position 339 of the ETH precursor sequence at Table 4. This ETH-PRP1 nucleic acid sequence is also provided at SEQ ID NO:19.

ETH-PRP2

An ETH-PRP2 peptide has also been identified by the present inventors. This peptide has been characterized as a 15-mer peptide, and constitutes a sequence within the ETH precursor. The amino acid sequence encoding the ETH-PRP2 is located upstream of the ET1PRP1 encoding amino acid sequence.

In one aspect, the ETH-PRP2 is defined as being encoded by an amino acid sequence essentially as defined by the sequence beginning at about amino acid Gln at position 20 through about amino acid Val at position 34 of the ETH precursor sequence (See Table 3). This amino acid sequence is also provided at SEQ ID NO:13.

It is possible that the ETH-PRP2 will also correspond to a slightly different amino acid sequence than the one defined at SEQ ID NO:13, and the nucleic acid sequences encoding the ETH-PRP2 having the amino acid sequence at SEQ ID NO:17.

The invention also provides a nucleic acid molecule for ETH-PRP2. In one embodiment, the nucleic acid molecule for ETH-PRP2 is defined as comprising a nucleic acid sequence encoding an ETH-PRP2 having an amino acid sequence essentially as defined at SEQ ID NO:13. In other embodiments, the ETH-PRP2 nucleic acid molecule comprises a nucleic acid sequence essentially as defined by the sequence beginning at about nucleic acid C at position 58 to about nucleic acid A at position 102 of an ETH precursor sequence as set forth at Table 4. This nucleic acid sequence is also provided at SEQ ID NO:17.

ANTISENSE STRATEGIES—ANTISENSE ETH, ETH PRECURSOR, ETH-PRP1, AND ETH-PRP2 PREPARATIONS

ETH has been found by the present inventors to disrupt development of all insect life stages, including larval, pupal, and adult stages, rendering insect population control by this strategy much more effective than previously proposed preparations. For example, ETH is shown here to elicit biological responses during a wide window of development, from first instar larval through to the adult stage. Arresting development and/or retarding maturation of insects using the novel preparations of the present invention thus provides an effective, broad scope preparation for reducing defoliation of crop plants and other economically detrimental activities related to insect feeding.

Antisense sequences (See example 26) to eclosion hormone (EH), ecdysis triggering hormone (ETH), receptors for these hormones, ETH-PRP1 and ETH-PRP2 are also provided as part of the present invention. In one aspect, these antisense sequences will be incorporated into insects and other sensitive organisms as part of a method for manipulating development, and for use as insecticides. These antisense compositions and methods of use constitute further embodiments of the present invention.

A purified mRNA molecule encoding an ecdysis triggering hormone having a sequence essentially as set forth in SEQ ID NO:18 and substantially free of mRNA not encoding the ecclysis triggering hormone is also presented here.

Nucleic acid molecules that encode a peptide having ecdysis triggering like activity are also presented. These nucleic acid molecules are described as being prepared by a particular process, and employs sequence information from SEQ ID NO:16 as a nucleic acid probe to identify cDNA encoding the molecules selected as encoding the ecdysis-active peptides.

INSECTICIDAL PREPARATIONS

The present invention will be particularly useful in the formulation and development of preparations for use in the control of insects. Some of these preparations, by way of example, are illustrated below.

In particular embodiments of the insecticidal preparations, a composition comprising as an active ingredient a substantially purified ETH precursor, ETH, ETH-PRP-1, ETH-PRP-2, or combination thereof, is provided, wherein said active ingredient is substantially free of associated polypeptide, is described.

TOPICAL PREPARATIONS

The ETH, ETH-PRP1, ETH-PRP2, ETH precursor,and bioactive peptide fragments thereof, may be formulated in DMSO, or other suitable carrier, to enhance the permeability of the preparation through insect cuticle. This preparation may then be applied as a spray or delivered into a water source as an insect control strategy.

Organic molecules identified through the screening assay for compounds that bind ecdysis triggering hormone receptor and/or eclosion hormone receptor may also be formulated for use as an insect spray, bait or water treatment.

TRANSFECTION

In one particular application, a sense, an antisense, or combination of sense and antisense sequences for one or a combination of the ETH, ETH-PRP1, ETH-PRP2, EC, ETH Precursor, or receptor binding molecules, will be engineered into a virus using standard techniques.

For use as an insecticide, the virus carrying the ETH or EH antisense sequence(s) will be formulated according to standard field application protocols, and then sprayed, by way of example, onto crops. The occluded virus (OV) is an example of a suitable virus carrier to be used in these applications, these viruses entering the insect via an oral route and solubilized in the alkaline midgut, thus releasing the embedded virions. The virions will enter the midgut cells and subsequently enter the hemocoel as budded virus (BV), and will then be transported to other tissues via the circulatory system and along the tracheal network via epidermal cells. The infection process will result in cessation of insect feeding within 5–7 days.

Application of antisense engineered sequences may be had to provide effective delivery of anti-hormone sequences to pest populations, and be expected to prevent successful insect molting.

In particular embodiment, viral constructs comprising sense sequences for ETH are provided, and comprise a sequence essentially as set forth in SEQ ID NO:16, which includes the sequences for the precursor ecdysis triggering hormone cDNA, have been prepared. Yet another particular embodiment of the viral vectors of the present invention comprises a sequence essentially as set forth in SEQ ID NO:25. Viral vectors with each of the sequences have been constructed using a baculovirus vector pACUW21. However, other vectors may be used together with these and other of the ETH-encoding sequences, and used in insecticidal preparations.

The utility of ETH, ETH-PRP1, ETH-PRP2 and functionally similar peptides may be optimized by transfection and expression of the corresponding artificial or native genes in viral, bacteria or other insect pathogens. Vectors will be packaged into an appropriate microbial delivery system for insect control, such as a virus or bacterium. A variety of vectors may be employed with the sequences for ETH and precursor related peptides in the practice of the invention, such as SF9, SF21, TN5, and HIGH5 cell lines.

In one particular construct, an SF21 vector construct has been prepared containing the ETH Manduca nucleic acid sequence. In specific constructs, the SF21 vector containing the nucleic acid sequence for ETH precursor may be prepared, in both truncated and non-truncated forms.

By way of example, a viral delivery system such as pAcUW2B under the control of a p10 promoter (Stewart et al., 1991) may also be used. Other viral systems, such as those described by Tomalski et al. (1991), and Maeda et al., (1991) also are considered useful in the practice of the present invention, these teachings also being specifically incorporated herein by reference.

The ETH, ETH-PRP1 and ETH-PRP2 encoding nucleic acid molecules of the present invention may also be used to transform plants. For example, these coding nucleic acid sequences may used either alone or in combination to transform vegetable and fruit plants. Such may be used as part of a method to enhance insect susceptibility to ecdysis triggering hormone like activity, particularly where it is co-expressed with a suitable gut-permeating agent, such as *Bacillus thuringiensis* toxins.

The ETH-encoding nucleic acid sequences may be formulated in microbial delivery systems for application to plants, animals, or both, as a spray or bait. Examples of these preparations are described below. The various topically active preparations that bind ETH receptor may be formulated directly into a spray or bait for use in the control of insects by applying to plants and animals.

AGRICULTURAL/URBAN APPLICATIONS

The ETH, ETH-PRP1, ETH-PRPR2, and its related homologs for agricultural use will be formulated in a manner appropriate for field application, as sprays, or baits, for release into aquatic environments, and for use in urban dwellings. Treatments for cockroaches, ticks, fleas, termites and other common pests may thus be conveniently and relatively easily provided using the preparations of the present disclosure.

Topically active preparations of the present invention for ETH, such as compounds that bind the ETH receptor identified using the Inka cell and ETH proteins described herein, may be formulated for application to agricultural crops and other plants to control insect populations, for example lepidopteran insect populations. Economic loss to a variety of important agricultural crops, including vegetable crops, cotton, grains, such as corn, wheat and soybeans, attributable to lepidopteran insects, may thus be reduced. Insecticides that include the compounds characterized using the present invention ETH provide a bioacceptable approach for controlling against loss attributable to many varieties of insects without toxicity to other animals and humans.

The peptide ETH is effective for inducing developmental effects when injected into the insect. For topically active formulations, the gene encoding the ETH or homolog or biologically active fragment thereof, will be included with a virus and the virus applied to crops (or animals) that are at risk of harboring the lepidopteran pests. Alternatively, the effectiveness of these preparations may be further enhanced by including within the virus a neurotoxin that will act to paralyze the virus. Additionally, ETH receptor binding molecules may be prepared as a topically active insecticide.

Techniques for enhancing the rate of viral replication of the ETH gene may also be employed. For example, see Maeda et al. ((1991), Virology, 184:777–780) and Tomalski et al. (1991) Nature, 352:82–88), both articles being specifically incorporated herein by reference for description of common techniques for enhancing the rate of viral replication.

LIVESTOCK APPLICATIONS

The protein or peptide fragments thereof may also be used to control pathogens that are transmitted by insects that are sensitive to the proteins/peptides. For example, the presently described peptide and proteins of ETH may be formulated for use in the control of insect (flies) and arachnid (ticks) parasites of livestock, as well as in the control of diseases carried by these animal groups.

Purification of ETH

Further aspects of the present invention concern the purification, and in particular embodiments, the substantial purification, of ETH. The phrase "purified ETH" as used herein, is intended to refer to a polypeptide composition, isolataible from lepidopteran insects wherein the ETH is purified to any degree relative to its naturally-obtainable state, i.e., in this case, substantially free of associated polypeptides. A purified ETH, therefore, also refers to isolated ETH, free from the environment in which it may naturally occur.

Generally, "purified" will refer to an ETH composition which has been subjected to fractionation to remove various non-polypeptide components, such as other non-ETH polypeptide and cell components, and which composition substantially retains its ability to induce ecdysis activity in vitro absent a tracheal system. Where the term "substantially purified" is used, this will refer to a composition in which ETH forms the major component of the composition, such as constituting from about 50% to about 60% of the protein in the composition or more.

Various methods for quantifying the degree of purification of the ETH will be known to those of skill in the art in light of the present disclosure. These include, for example, determining the specific activity of an active fraction, or assessing the number of polypeptides within a fraction by SDS/PAGE analysis. A preferred method for assessing the purity of an ETH fraction is to calculate the specific activity of the fraction, to compare it to the specific activity of the initial ETH source (e.g., Lepidopteran insect perisperacular glands), and to thus calculate the degree of purity, herein assessed by a "-fold purification number."

The actual units used to represent the amount of ecdysis triggering activity will, of course, be dependent upon the particular assay technique chosen to follow the purification. As discussed above, the present inventors prefer to use an assay based upon time for induction of ecdysis of a lava, pupa or adult lepidopteran insect, or for stimulating ecdysis activity in nervous tissue absent a tracheal system in vitro.

As is generally known in the art, to determine the specific activity, one would calculate the number of units of activity per milligram of total protein. In the purification procedure, the specific activity of the starting material, i.e., of the epitracheal glands containing ETH, would represent the specific activity of the ETH in its natural state. At each step, one would generally expect the specific activity of the ETH to increase above this value, as it is purified relative to its natural state. In preferred embodiments, it is contemplated that one would, assess the degree of purity of a given ETH fraction by comparing its specific activity to the specific activity of the starting material, and representing this as X-fold purification. The use of "-fold purification" is advantageous as the purity of a biologically active fraction can thus be compared to another despite any differences which may exist in the actual units of activity or specific activity.

It is contemplated that the ETH and its related peptides, ETH-PRP1 and 2, of the present invention be purified to between about 60-fold and about 80-fold, and preferably, of between about 90-fold and about 100-fold, or in even other embodiments, to about 1000-fold, relative to its natural state. As most proteins are not expressed at more than 0.05 to 0.5% of total protein in a tissue, the preparations of the present invention are significantly purified relative to the naturally occurring state of ETH.

The physiological concentration of ETH in pharate pupae *Manduca sexta* has been calculated to achieve as an upper limit a concentration in the circulation system following release from epitracheal glands, of about 180 nM. In some embodiments, the preparations of the invention defined as purified "relative to the naturally occurring state" of ETH relates to preparations comprising concentrations of ETH greater than about 180 nM. These preparations may also be defined as substantially free of associated polypeptides.

In one embodiment, to prepare a substantially purified ETH in accordance with the present invention one would concentrate an insect extract by ultrafiltration of the lepidopteran insect preparation followed by DEAE-cellulose-anion-exchange chromatography, ultra gel ACA54 gel filtration chromatography, wheat-germ agglutinin agarose chromatography, and reverse phase chromatography. Analysis of purified ETH or the related peptide is then done to quantify biological activity using relative time for induction of ecdysis activity as an indicator.

In yet another particular embodiment, the method for preparing an ecdysis triggering hormone purified relative to its naturally occurring state comprises extracting endocrine or neuroendocrine insect tissue to provide an insect extract; and obtaining ecdysis-triggering active fractions comprising an ecdysis triggering hormone purified relative to its naturally occurring state, said hormone having a molecular weight of about 2000 Da to about 3500 Da as determined by liquid secondary ion mass spectrometry. In one aspect of the practiced method, the insects to be extracted are further defined as comprising lepidopteran insects.

Various techniques suitable for use in protein purification will be well known to those of skill in the art. These include, for example, purification through use of anti-ETH antibody and the like, or by heat denaturation, followed by centrifugation, chromatography steps such as ion exchange, gel filtration, reverse phase, hydroxylapatite and affinity chromatography; isoelectric focusing; and combinations of such and other techniques. A specific example presented herein is the purification of ETH using reversed phase liquid (RPLC) chromatography of endocrine glands extracted from pharate pupa at a stage about 8 hours preceding natural ecdysis.

Although preferred for use in certain embodiments, there is no general requirement that the ETH always be provided in its most-purified state. Indeed, it is contemplated that less substantially purified ETH, which is nonetheless enriched in ETH activity relative to the natural state, will have utility in certain embodiments. These include, for example, the induction of ecdysis motor behavior from isolated nerve cord preparations absent a tracheal system. Partially purified ETH fractions for use in such embodiments may be obtained by subjecting gland extracts from lepidopteran or other insect supernatant to one or a combination of the steps described here.

Reverse Phase Liquid Chromatography of ETH

The ETH of the present invention is particularly characterized as comprising a polypeptide as determined by reverse phase liquid chromatography to have a molecular weight of about 2940 Da. In one particular embodiment, the ETH of *Manduca sexta* has a molecular weight of 2940.45 daltons as determined by liquid secondary ion mass spectrometry (LSIMS), electrospray mass spectrometry (ES-MS) and laser desorption-time of flight mass spectrometry (LDTOF-MS). However, it is, of course, generally understood by those of skill in the art that evolution of insects has created some variability in the gene coding for the peptide, such that molecular weights of the ETHs of various insect groups will fall in the range of about 2000 to about 3500 daltons.

Based on the studies provided here, those of ordinary skill in the art will appreciate that the examples of ETH herein disclosed comprise an ancestrally related family of developmentally important peptides/proteins.

It will be further understood that certain of the polypeptides may be present in quantities below the detection limits of the Coomassie brilliant blue staining procedure usually employed in the analysis of SDS/PAGE gels, or that their presence may be masked by an inactive polypeptide of similar molecular weight. Although not necessary to the routine practice of the present invention, it is contemplated that other detection techniques may be employed advantageously in the visualization of each of the polypeptides present within the hormone. Immunologically-based techniques such as Western blotting using enzymatically-, radiolabel-, or fluorescently-tagged secondary antibodies are considered to be of particular use in this regard.

The preferred purification method disclosed herein contains several steps and represents the best mode presently known by the inventor to prepare a substantially purified ETH. This method is currently preferred as it results in the substantial purification of the ETH polypeptide, as assessed by RPLC, in yields sufficient for further characterization and use. This preferred mode of ETH purification involves the execution of certain purification steps in the order described herein below. However, as is generally known in the art, it is believed that the order of conducting the various purification steps may be changed, or that certain steps may be omitted, and still result in a suitable method for the preparation of a substantially purified ETH.

The ETH proteins of the invention may be isolated from essentially any insect endocrine tissue or fluid (e.g., such as the epitracheal glands and hemolymph prior to ecdysis in the insect). The epitracheal glands (EG) of lepidopteran insects, such as the tobacco hornworm, *Manduca sexta*, are one example of the endocrine organs that have been found by the present inventors to be a source of ETH protein. It is expected that the protein, and closely related substances and analogs of ETH, may be obtained from other insect organs and fluids that comprise the endocrine system. These organs, by way of example, include the gut and nervous system.

Virtually any insect that has as part of its life cycle a molting event, whereby the skin or exoskeleton of the insect is shed, may be used to provide the ETH peptide, and further developmentally regulated with ETH. Extract prepared from any insect having this developmental event is expected to contain the peptide/protein materials herein described that are capable of modifying the normal developmental process of the insect.

For example and not by exclusion, in addition to Manduca and Bombyx, it is expected that the peptide/protein may be isolated from Coleoptera, Hemiptera, Homoptera, Diptera, and Orthoptera species.

HOST CELLS AND VECTORS

The present invention provides a number of recombinant host cells and viral vectors comprising the ETH and ETH-PRP1 and ETH-PRP2, sequences herein disclosed.

As used herein, the term "engineered" or "recombinant" cell is intended to refer to a cell into which an exogenous DNA segment or gene, such as a cDNA or gene encoding an ecdysis triggering hormone has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinantly introduced genes will either be in the form of a cDNA gene (i.e., they will not contain introns, See SEQ ID NO:16), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

The artificial gene for ETH and related peptides has been constructed by chemical synthesis and incorporated into suitable expression vectors.

Prokaryotic hosts are preferred for expression of the ETH protein, peptide and analog thereof. An example of a prokaryotic host which is particularly useful is *E. coli* strain M15[pREP4] and SG13009[pREP4]. Enterobacteriaceae species such as *Salmonella typhimurium* and *Serratia marcescens*, various *Pseudomonas species*, or gram-positive bacilli such as *Bacillus subtilus* may also be used.

In general, plasmid vectors containing replicon and control sequences which are derived from species compatible with the host cell are used in connection with these hosts.

The vector ordinarily carries a replication site, as well as marking sequences which are capable of providing phenotypic selection in transformed cells. For example, *E. coli* is typically transformed using pBR322 (Bolivar et al., 1977), or one of its many derivatives. PBR322 contains genes which express ampicillin and tetracycline resistance in Gram-negative hosts and thus provides easy means for identifying transformed cells. PBR322, its derivatives, or other microbial plasmids or bacteriophage may also contain, or be modified to contain, promoters which can be used by the microbe for expression of endogenous proteins.

In addition, phage vectors containing replicon and control sequences that are compatible with the host microorganism can be used as transforming vectors in connection with these hosts. For example, bacteriophage such as >GEM-11n may be utilized in making a recombinant vector which can be used to transform susceptible host cells such as *E. coli* LE392.

Those promoters most commonly used in recombinant DNA construction include the β-lactamase (penicillinase) and lactose promoter systems (Change et al., 1978; Itakura et al., 1977; Goeddel et al., 1979) or the tryptophan (trp) promoter system (Goeddel et al., 1980; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (EPO Appl. Publ. No. 0036776).

In addition to prokaryotes, eukaryotic microbes, such as yeast cultures may also be used. *Saccharomyces cerevisiae*, or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC No. 44076 or PEP4-1 (Jones, 1977). The presence of the trpL lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated in the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts. In principle any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

cDNA for ETH cDNA was prepared from the total mRNA isolated from epitracheal glands and a cDNA encoding the precursor for ETH was isolated and characterized using oligonucleotide probes, polymerase chain reaction, and other suitable approaches leading to the cloning of the native ETH gene. A cDNA expression library prepared from epitracheal glands, and the precursor encoding ETH has been isolated using labelled oligonucleotide probes, PCR and antibodies against ETH and related peptides. The native cDNA precursor encoding ETH will be subcloned into suitable expression vectors, and used as described herein.

PRODUCTION OF RECOMBINANT ETH

For the expression of the gene encoding ETH, once suitable (full-length if desired) clone(s) are obtained, whether they be cDNA based, or genomic, one may prepare an expression system for the recombinant preparation of ETH. The engineering of DNA segment(s) for expression in a prokaryotic system may be performed by techniques generally known to those of skill in recombinant expression. It is believed that virtually any expression system may be employed in the expression of ETH.

ETH may be successfully expressed in bacterial yeast or baculovirus expression systems may ultimately be preferred for the preparation of ETH for all purposes. The cDNA for ETH may be separately expressed in bacterial systems, with the encoded proteins being expressed as fusions with β-galactosidase, ubiquitin, *Schistosoma japonicum* glutathione S-transferase, and the like. It is believed that bacterial expression will ultimately have numerous advantages, ease of use and quantity of materials obtained thereby.

It is proposed that transformation of host cells with DNA segments encoding ETH will provide a convenient means for obtaining biologically active protein and peptides. However, separate expression followed by reconstitution is also certainly within the scope of the invention. Both cDNA and genomic sequences are suitable for eukaryotic expression, as the host cell will, of course, process the genomic transcripts to yield functional mRNA for translation into protein.

It is similarly believed that almost any eukaryotic expression system may be utilized for the expression of ETH (e.g., baculovirus-based, glutamine synthase-based or dihydrofolate reductase-based systems could be employed). For example, plasmid vectors incorporating an origin of replication and an efficient eukaryotic promoter, as exemplified by the eukaryotic vectors of the pCMV series, such as pCMV5, will be of use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e. 3' of) the chosen promoter.

Where eukaryotic expression is contemplated, one will also typically desire to incorporate into the transcriptional unit which includes the enzyme, an appropriate polyadenylation site (e.g., 5'-AATAAA-3') if one was not contained within the original cloned segment. Typically, the poly-A site is placed about 30 to 2000 nucLeotides "downstream" of the termination site of the protein at a position prior to transcription termination.

It is contemplated that virtually any of the commonly employed host cells can be used in connection with the expression of ETH in accordance herewith. Examples include cell lines typically employed for eukaryotic expression such as FLS4.1, 239, X63Ag8, AtT-20, HepG2, VERO, HeLa, CHO, WI 38, BHK, COS-7, 558L, RIN and MDCK cell lines.

It is contemplated that the ETH polypeptide of the invention may be "overexpressed," i.e., expressed in increased levels relative to its natural expression in lepidopteran insect cells, or even relative to the expression of other proteins in the recombinant host cell. Such overexpression may be assessed by a variety of methods, including radiolabeling and/or protein purification. However, simple and direct methods are preferred, for example, those involving SDS/PAGE and protein staining or Western blotting, followed by quantitative analysis, such as densitometric scanning of the resultant gel or blot. A specific increase in the level of the recombinant protein or peptide in comparison to the level in natural lepidopteran insect cells is indicative of overexpression, as is a relative abundance of the specific protein in relation to the other proteins produced by the host cell as determined by methods such as gel electrophoresis.

As used herein, the term "engineered" or "recombinant" cell is intended to refer to a cell into which an exogenous DNA segment or gene, such as a cDNA or gene encoding ETH or its related precursor peptides, has been introduced. Therefore, engineered cells are distinguishable from naturally occurring cells which do not contain a recombinantly introduced exogenous DNA segment or gene. Engineered cells are thus cells having a gene or crenes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

ANTIBODIES TO ETH

Provided are methods for generating antibodies specific for ETH. Such antibodies find utility in screening for ETH and crossreactive species. The peptide and proteins of the invention has been used to generate antibodies. Both polyclonal and monoclonal are contemplated as part of the invention. These antibodies have several applications, including, by way of example and not exclusion, in a screening method for selecting candidate substances having ecdysis-triggering hormone like activity, candidate substances that demonstrate binding affinity to the antibody being selected as a candidate substance having ecdysis triggering activity.

The antibodies of the present invention in particular embodiments are further described as having binding affinity for ETH, ETH precursor, ETH-PRP1, or ETH-PRP2, or a combination thereof, and as without binding affinity for eclosion hormone.

POLYCLONAL ANTIBODIES

Immunization of New Zealand white rabbits (female, under 8 lbs) was conducted on a 3-week schedule. A 1:1 mixture of 200 mg ETH peptide and Freund's complete adjuvant was used for the initial immunization; 10–12 injections are made intradermally in the shoulder region of the rabbit. Booster injections followed at 3 week intervals with equal proportions of ETH (20–200 mg) and Freund's incomplete adjuvant. Serum was taken prior to each boost and tested for the presence of circulating antibodies to ETH by ELISA. Specificity is tested by comparing serum responses to ETH and other peptides, such as eclosion hormone, crustacean cardioactive peptide, proctolin, pheromone biosynthesis activating hormone, small cardioactive peptide, etc.

Alternatively, Balb/c mice of approximately 3 months in age may be immunized intraperitoneal (day 0) with 10 to 50 Hg./mouse of the ETH homogenized with a suitable adjuvant system. The mice will then be given two consecutive weekly intraperitoneal injections of the antigens mixed with the selected adjuvant (day 7 and 14). Approximately one month after the third injection, booster inoculation of antigens alone may be given. Here the inventors contemplate that the novel booster method described below will be advantageously employed. It is proposed that the immunized mice may be surgically opened to expose the spleen and a sterile solution of 5 to 20Hg of the ETH antigens will be injected directly into the spleen. The mouse will then be sutured and allowed to recover. It is believed that this method will allow the optimal exposure of the splenocytes to the booster antigen.

Five to 7 days after the booster injection, a small amount of blood from the tail of the immunized mice will be bled and tested for the presence of circulating antibodies to ETH by an enzyme-linked immunosorbent assay (ELISA).

MONOCLONAL ANTIBODIES

Mice treated as outlined above that produce reasonable titers of circulating antibodies to the partially purified antigens will be sacrificed and their spleens will be aseptically removed for cell fusion.

The mouse myeloma cell line proposed to be of use for hybridization is the 8-azaguanine-resistant mouse murine myeloma SP2/0 non-producer cell line. The SP2/0 cell line has been selected for 8-azaguanine resistance and does not survive in medium containing hypoxanthine, aminopterin, and thymidine (HAT). The cells will be fused as described in (Chan et al., 1987). Immune splenocytes ($10^8$ cells) obtained from two hyperimmunized mice and 8-azaguanine-resistant SP2/0 mouse myeloma cells ($10^7$ cells) will be fused using 37% (v/v) polyethylene glycol 1500 (M. W. 500–600 M. A. Bioproducts, Inc.). Fused cells will be maintained for two days in growth medium that has been conditioned by SP2/0 cells, and then plated in five or six 96-well microtiter plates in growth medium containing HAT (selection medium) and screened for antibody production at the end of 2 weeks by indirect ELISA.

For the screening, purified ETH, or partially purified ETH obtained from insect endocrine or neuroendocrine tissues and organs, such as the epitracheal glands of lepidopteran insects, may be used as target antigens, and proctolin, crustacean cardioactive peptide, or enkephalin as controls. The target antigens (50 ng/50H/well) may be immobilized onto the bottoms of the 96-well microtiter plates at 4° C. overnight. The culture medium from the wells propagating the splenocyte-myeloma (hybridoma) cells growing in the selection medium may be assayed for secreted antibodies that react with the immobilized antigens. The isotypes of the immunoglobulin(s) produced by cloned hybridoma cell clones may also be determined by ELISA, employing a commercial isotyping kit. The specificity of the mAbs may be determined by their reactivity with various antigens, as examined by ELISA and confirmed by western blot analysis.

After the mAbs are characterized, they may be produced in the form of mouse ascites fluid, purified and used to antagonize the soft agar colony forming efficiency, inhibit cellular activation, immunofluorescence staining, immunohistochemistry, and ELISA. This assay is proposed to be a reproducible, convenient and rapid assay method.

Immunoassays

Turning first to immunoassays, in their most simple and direct sense, preferred immunoassays of the invention include the various types of enzyme linked immunosorbent assays (ELISAs) known to the art. However, it will be readily appreciated that the utility of ETH peptides is not limited to such assays, and that other useful embodiments include RIAs and other non-enzyme linked antibody binding assays or procedures.

In one such ELISA, peptides incorporating the ETH antigen sequences of invention may be first immobilized onto a selected surface, e.g., a well of a surface exhibiting a protein affinity, such as a well in a polystyrene microtiter plate. In such an ELISA, generally, labelled anti-ETH antibodies would then be added to the wells, allowed to bind, and detected by means of their label. The amount of ETH in an unknown sample would be determined by mixing the sample with the labeled anti-ETH antibodies before or during incubation in an appropriate container means.

In another form of ELISA, an antibody capable of binding an ETH protein or peptide of the invention may be immobilized onto the solid surface, or well, and used directly in conjunction with labeled ETH compositions. In these ELISAs, generally, labeled ETH is added to the wells, allowed to bind, and detected by means of the label. The amount of ETH in an unknown sample is here determined by mixing the sample with the labeled ETH before or during incubation with the ETH antibody in the wells. The presence of ETH in the sample again acts to reduce the amount of labeled ETH available for binding to the well, and thus reduces the ultimate signal.

In coating a plate with either antigen or antibody, one will generally wash the wells of the plate to remove incompletely absorbed material and then bind or "coat" a nonspecific protein onto the wells of the plate. Nonspecific proteins are those that are known to be antigenically neutral with regard to the test antisera, and include bovine serum albumin (BSA), casein and solutions of milk powder. The coating allows for blocking of nonspecific absorption sites on the immobilizing surface and thus reduces the background caused by nonspecific binding of the antisera onto the surface.

Where an antibody capable of binding an ETH polypeptide is immobilized onto an ELISA plate, it is more customary to use a secondary or tertiary detection means rather than a direct procedure. Thus, after binding of antibody to the well, coating with a non-reactive material to reduce background, and washing to remove unbound material, the immobilizing surface is contacted with the control ETH and/or clinical or biological sample to be tested in a manner conducive to immune complex (antigen/antibody) formation. Detection of the ETH then requires a labeled secondary antibody, or a secondary antibody and a labeled tertiary antibody. The labeled secondary antibody is, of course, an anti-ETH antibody that is conjugated to a detectable label. When using a tertiary approach, the secondary antibody is an unlabeled anti-ETH antibody and the tertiary antibody is a labeled antibody that is specific for the species, or isotype, of the secondary antibody employed.

A "manner conducive to immune complex (antigen/antibody) formation" means that the conditions preferably include diluting the antigens and antibodies with solutions such as BSA, bovine gamma globulin (BGG) and phosphate buffered saline (PBS) /Tween®. These added agents also tend to assist in the reduction of nonspecific background.

Incubation steps are typically from about 1 to 2 to 4 hours, at temperatures preferably on the order of 25° C. to 270° C., or may be overnight at about 40° C. or so. Following all incubation steps in an ELISA, the contacted surface is washed so as to remove non-immunocomplexed material. A preferred washing procedure includes washing with a solution such as PES/Tween, or borate buffer.

Following the formation of specific immunocomplexes between the test sample and the originally bound material, and subsequent washing, the occurrence of even minute amounts of immunocomplexes may be determined. As mentioned above, this may be achieved by subjecting the first immunocomplex to a second antibody having specificity for the fist, or even a third antibody having specificity for the second. Where a second antibody alone is used, given that the control and test ETH samples will typically be of insect origin, the second antibody will preferably be an antibody having specificity in general for the insect ETH. Where a third antibody is also used, the second antibody will still preferably be an antibody having specificity ETH, and the third antibody will then be an antibody having specificity in general for the second antibody. A second rabbit antibody and a third anti-rabbit Ig antibody is a particular example.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunocomplex with a urease, glucose oxidase or peroxidase-conjugated antibody for a period of time and under conditions that favor the development of further immunocomplex formation (e.g., incubation for 2 hours at room temperature in a PBS-containing solution such as PES-Tween).

After incubation with the labeled antibody, and subsequent t washing to remove unbound material, the amount of label is quantified, e.g., by incubation with a chromogenic substrate such as urea and bromocresol purple or 2,2'-azino-di-(3-ethylbenzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

ANTI-ETH HORMONE

The present inventors also envision the synthesis of anti-ETH hormone agents, such as in the form of an antisense oligonucleotide, that could be used to halt ecdysis and/or pre-ecdysis behaviors by preventing the production of ecdysis triggering hormone, and/or reducing these behaviors by inhibiting ETH-PRP1, ETH-PRP2, or any combination of these.

Antisense sequences to the ETH precursor cDNA, EC, ETH, ETH-PRPI ETH-PRP2, or to receptor of EC or ETC, would include a sequence capable of binding the nucleic acid sequences encoding these respective substances. These antisense sequences are noted at the sequences essentially as defined at SEQ ID NO:20 (DNA-ETH Precursor), 21 (cDNA for ETH Precursor), 22 (ETH), 23 (ETH-PRP1) and 24 (ETH-PRP2)

SILK PRODUCTION APPLICATIONS

The compositions of the present invention may also be used in a method for enhancing silk production and yields thereof. These applications are described more fully herein, and comprise generally the use of the ETH, either alone or with other hormones (e.g., juvenile hormone and antibiotics) for improved cultivation methods of silkworms.

SYNCHRONIZATION OF MOLTING BEHAVIORS—COMMERCIAL APPLICATIONS

Production of animals at particular developmental stages is important in several industries, including the silk industry as discussed above, as well as in businesses that rely on the ready availability of particular animals, such as in the availability of soft-shell crab.

In yet another aspect of the invention, a method for synchronizing the developmental stage of a population of animals is provided. In one embodiment, the method comprises administering an ecdysis triggering amount of a composition comprising ecdysis triggering hormone or its related peptide, ETH-PRP1 or 2, substantially free from associated polypeptide to a population of animals. This method is expected to provide a population of animals in a substantially synchronized developmental stage.

RECEPTOR SCREENING ASSAY 1. Use of ETH to identify and clone its receptor ETH will, be derivatized and used as a probe to identify ETH receptor. Messenger RNA will be prepared from the insect nervous system, reverse-transcribed to provide a cDNA, and cDNA fragments thereof incorporated into an expression library using COS cells.

In one aspect of the screening method, a cell line expressing an ecdysis triggering hormone receptor will be used. The cell line expressing an ecdysis triggering hormone receptor may be defined by reference to the process by which it will be obtained. This process comprises extracting insect endocrine or neuroendocrine tissue and obtaining mRNA, reverse transcribing the mRNA to provide cDNA; preparing a cDNA vector library from said cDNA; transforming cells capable of expressing an ecdysis triggering hormone receptor gene with cDNA vector library to provide transformed cells; exposing said transformed cells to a detectably labeled ecdysis triggering hormone comprising of a sequence essentially as set forth in SEQ ID NO:15; and selecting transformed cells that bind the labeled hormone to provide cells expressing the ecdysis triggering hormone receptor.

In one particular embodiment, the cell line transformed to express the ecdysis triggering hormone receptor comprise COS (particularly COS-7) cells. There are several expression vectors that may be used in this process. By way of example, such expression vectors include pcDNA3 or pcDM8.

The ecdysis triggering hormone receptor itself may also be used and prepared according to the present invention. The ecdysis triggering hormone receptor may be obtained by a process comprising obtaining a cDNA vector library of insect endocrine and neuroendocrine tissues; transforming cells capable of expressing an ecdysis triggering hormone receptor gene to provide transformed cells; exposing said transformed cells to a detectably labeled ecdysis triggering hormone comprising a sequence essentially as set forth in SEQ ID NO:15, or a hybridizable portion thereof; selecting transformed cells that bind the detectibly labeled hormone as cells expressing the ecdysis triggering hormone; and purifying ecdysis triggering hormone receptor from the cells expressing the ecdysis triggering hormone.

A CDNA encoding an ecdysis triggering hormone receptor is also provided, and may similarly be used in various aspects of the receptor screening assay. In one embodiment, the cDNA encoding an ecdysis triggering hormone receptor is obtained by a process comprising extracting the ecdysis triggering hormone receptor described above, (or from a transformed cell expressing the ETH receptor), and sequencing an amino acid fragment of the ecdysis triggering hormone receptor; preparing a nucleotide (oligonucleotide) probe having a sequence encoding the amino acid fragment of the ecdysis triggering hormone receptor; isolating cDNA from cells expressing the ecdysis triggering hormone transformed cells as described above; screening the cDNA with the nucleotide probe; and selecting cDNA hybridizing to the nucleotide probe as the cDNA encoding ecdysis triggering hormone receptor. The hybridization conditions employed in these assays will be standard hybridizing conditions as described herein.

2. Use of the ETH receptor as a screening strategy for small organic molecules as contact insecticides.

The ETH receptor will be expressed in a cell line and coupled to a suitable signal transduction pathway and reporter genes. This system will be used for large-scale screening assays in the identification of organic molecule insecticides that act to disrupt the ETH signaling system.

In one particular embodiment, a screening assay for organic molecules that bind ecdysis triggering hormone receptor comprises preparing the ecdysis triggering hormone receptor cDNA as described above, incorporating the ecdysis triggering hormone receptor cDNA into a plasmid; transforming a cell line with the plasmid to provide a transformed cell line expressing the ecdysis triggering hormone receptor; exposing the transformed cell line to candidate receptor binding molecules; and selecting organic molecules that compete with ecdysis triggering hormone having a sequence essentially as set forth in SEQ ID NO.2 or 3 for binding to the transformed cells.

In another embodiment of the screening method, the screening assay for organic molecules that bind ecdysis triggering hormone receptor comprises exposing the ecdysis triggering hormone receptor as isolated in the descriptive process above, to candidate receptor binding molecules; and selecting candidate substances that compete with ecdysis triggering hormone having a sequence essentially as set forth at SEQ ID NO.2 or 3 to the ecdysis triggering hormone receptor, as organic molecules that bind ecdysis triggering hormone receptor.

It is expected that candidate substances which bind the ETH receptor will be relatively small and lipophilic. Such molecules may be easily formulated into pesticidal compositions comprising these organic molecules that bind the ecdysis triggering hormone receptor described here, and posses enhanced surface activity relative to protein/peptide containing compositions.

3. Eclosion Hormone Receptor

Methods for identifying and using the receptor for eclosion hormone also constitute embodiments of the present invention. The EH receptor will then be used as part of a screening assay to select for organic molecules that bind EH receptors. As generally described, such molecules that bind EH receptor will be relatively uncharged and lipophilic. The identified substances will be expected to process enhanced surface permeability, rendering insecticidal preparations comprising these identified substances capable of penetrating insect cuticle, improving contact insecticidal activity.

In one embodiment, the screening assay for organic molecules that bind eclosion hormone receptor will follow generally the same steps discussed above in relation to ecdysis triggering hormone. The screening assay is described in greater detail in the examples which follow.

Insecticidal compositions which include the organic molecules which bind eclosion hormone may also be conveniently formulated in an insecticidal composition and used commercially for control of insects. Techniques for formulating such a composition are well known to those of skill in the art.

4. Protean Purification Step

In order to obtain a cDNA encoding the eclosion hormone receptor or ecdysis triggering hormone receptor, the respective receptor must first be isolated and a protein fraction of the receptor obtained and at least in part sequenced (amino acid). The following text outlines one embodiment of the protein purification process.

ETH Receptor cDNA

To purify the protein for ETH receptors, one would first extract insect endocrine or neuroendocrine tissue and obtain a protein fraction. The protein fraction is then to be solubilized using a detergent.

The ecdysis triggering hormone receptor obtained by the process described above is purified, by way of example, by a combination of gel filtration chromatography, ion exchange chromatography, hydrophobic interaction chromatography, affinity chromatography using a sequence essentially as set forth in SEQ ID NO:15 (amino acid sequence for ETH precursor), and HPLC using reverse phase chromatography. Preferably, the N-terminus of the purified ecdysis triggering hormone receptor obtained, and the amino acid sequence of the N-terminal fragment will be used to design appropriate nucleotide (oligonucleotide) probes. The probes will then be used to screen a cDNA library derived from insect endocrine or neuroendocrine tissue. Positive clones comprising the cDNA for the receptor will then be identified and the ecdysis triggering hormone receptor cDNA isolated therefrom.

EH (Eclosion Hormone) Receptor cDNA

The same general process used for ETH will be used to obtain the cDNA for eclosion hormone, using Inka cells, neuroendocrine or endocrine insect tissue as a source tissue.

The cDNA sequence for eclosion hormone is described by Howadyski, et al. (1993), *P.N.A.S.* 86:8123–26.

Generally, the procedure for obtaining the ETH receptor above, will be used to obtain the EH receptor. A protein fragment, preferably an N-terminal fragment, of the EH receptor will then be sequenced, and used in preparing a nucleotide (oligonucleotide) probe. These probes will be used to screen a cDNA library from neuroendocrine, or endocrine tissue, or Inka cells. From this screening process, a clone containing the EH receptor cDNA will be selected, and the cDNA isolated.

The following abbreviations are used throughout the description of the present invention:

Mas-ETH=*Manduca sexta* ecdysis triggering hormone

ETH=ecdysis triggering hormone precursor

ETH-PRP1=ecdysis triggering hormone gene related peptide-one

ETH-PRP2:=ecdysis triggering hormone gene related peptide-two

EG=epitracheal gland

EC=eclosion hormone

Bom-ETH=*Bombyx mori* ecdysis triggering hormone

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Isolation and identification of ecdysis triggering hormone (Mas-ETH) from epitracheal glands. Reversed-phase liquid latency between 35 EG extracted from pharate pupae at about 8 hr preceding natural ecdysis. Mas-ETH (arrow) elutes at 55 min. The dotted line depicts the acetonitrile gradient shown on the right ordinate. Injections of pharate 5th instar larvae with 2 EG equivalents of this peak produced pre-ecdysis within 3 to 5 min.

FIG. 1B HPLC elution profile of 1 nmol of synthetic Mas-ETH.

FIG. 1C Elution profile of a mixture of 1 nmol synthetic and 0.5 nmol native Mas-ETH, showing co-elution. Methods were as described in Example 1.

FIG. 2A. Pre-ecdysis behavior (PE, natural) of the pharate 5th instar larva under natural conditions shows a dorsoventral contraction occurring synchronously in all segments every 10 to 12 sec, each contraction lasting for about 5 sec. A similar rhythm (PE, Mas-ETH) arose within 2 to 10 min of injection with 50 pmol synthetic Mas-ETH. The ETH synthetic hormone was injected 8 hours prior to natural ecdysis. Ecdysis behavior, consisting of anteriorly-directed peristaltic waves occurs about 1 hr after initiation of natural pre-ecdysis behavior or 35 to 50 min after Mas-ETH induced pre-ecdysis behavior. E (natural) shows natural ecdysis behavior, while E (Mas-ETH) depicts ecdysis behavior resulting from injection of Mas-ETH. Pre-ecdysis and ecdysis behaviors were recorded by in vivo blood pressure measurements during natural behavior (natural) or induced by injection of Mas-ETH (Mas-ETH). Calibrations: horizontal, 30 sec; vertical, 5 kilopascals.

FIG. 2B Pre-ecdysis (PE) and ecdysis (E) in the pharate pupa stage under natural conditions (natural) or following injection of 400 pmol synthetic Mas-ETH (Mas-ETH). Injections were made at 8 hr prior to natural ecdysis. The pre-ecdysis rhythm under natural conditions shows contractions every 3 to 4 seconds. Pre-ecdysis behavior is shown from the pharate pupa following injection of Mas-ETH (Mas-ETH). E (natural): ecdysis behavior under natural conditions and following injection of Mas-ETH (E, Mas-ETH). Pre-ecdysis and ecdysis behaviors were recorded by in vivo blood pressure measurements during natural behavior (natural) or induced by injection of Mas-ETH (Mas-ETH). Calibrations: horizontal, 30 sec; vertical, 5 kilopascals.

FIG. 3A–3 B Motor neuron burst patterns corresponding to pre-ecdysis and ecdysis behaviors recorded from the isolated central nervous systems of pharate 5th instar larvae under natural conditions or following application of synthetic Mas-ETH to the bath. Suction electrode recordings were made from the dorsal nerves of abdominal ganglia A5, A6, and A7 in each instance. Set of 3 traces shows pre-ecdysis burst pattern., characterized by synchronous bursting of motor neurons under natural conditions (3A) or following bath application of 100 nM synthetic MasETH (3B). Bursts of 5–7 sec are recorded every 10–15 sec in each instance.

FIG. 3C–3D Set of 3 traces shows ecdysis output patterns in pharate 5th instar larvae under natural conditions (3C) or after occur with a delay between segments of about 10 sec, demonstrating the peristaltic nature of the ecdysis motor program.

FIG. 3F–3F Set of 3 traces showing ecdysis behavior in the pharate pupal stage under natural conditions (3E) or after bath application of 5 mM MasETH (3F). Calibration bars: horizontal–10 sec; vertical: 10 mV.

DETAILED DESCRIPTION OF THE PREFERRED EMBODIMENTS

Figure 1A:
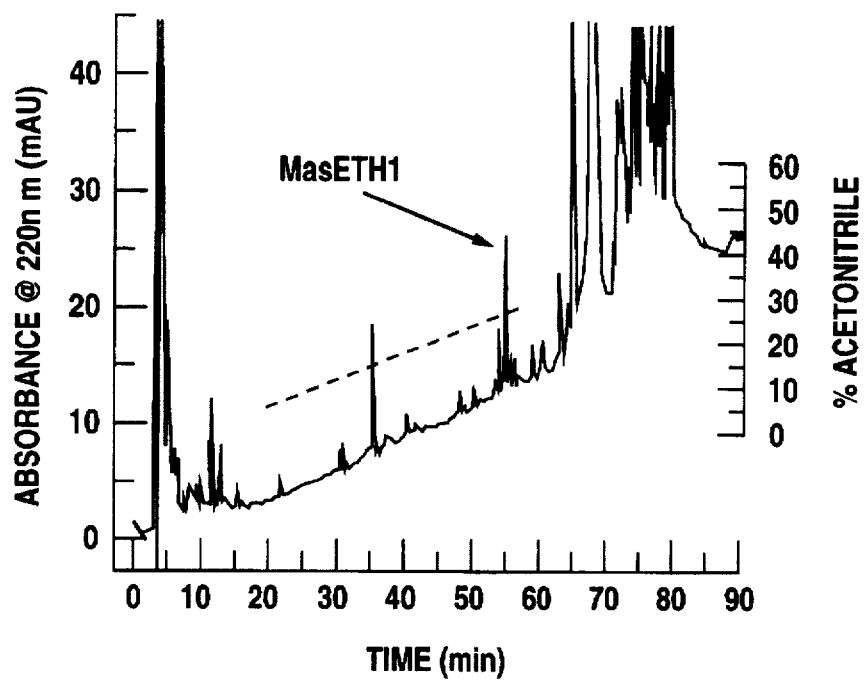

An endocrine system exists in lepidopterous insects, such as the *Manduca sexta*, Bombyx mori, *Heliothis virescens* and other insects. This endocrine system, found to occur in all larval, pupal and adult life stages, consists of 9 segmentally paired "epitracheal glands" (EG). The EGs are attached to the outer wall of the large tracheal tube near its connection with each segmented spiracle. Each EG contains 3–4cells, one of which is peptidergic and is called an "Inka cell".

The present inventors have identified a novel "ecdysis triggering hormone" (ETH), which was initially discovered to be released from InKa cells in response to eclosion hormone.

In one embodiment, the peptide may be derived from insects, such as from the tobacco hornworm, *Manduca sexta*. ETH, in one particular embodiment, comprises a protein containing 26 amino acids. In particular, this is: SNEAISPFDQGMMGYVIKTNKNIPRM, (SEQ ID NO:3). In particular applications, this ETH protein is amidated at the carboxy terminus.

As already noted, the ETH has been found by the inventors to be produced by a segmentally distributed endocrine system of epitracheal glands (EG) in *Manduca sexta*. These EG endocrine glands undergo a marked reduction in volume, appearance, and immunohistochemical staining during ecdysis, at which time the ETH may be found in the hemolymph. Injection of EG extract or synthetic ETH into pharate larvae, pupae or adults initiate pre-ecdysis in insects within 2 to 10 minutes followed by ecdysis.

The ETH disclosed here is distinct from other hormones, such as eclosion hormone, in several respects. For example, sensitivity to injected ETH appears much earlier prior to ecdysis and occurs with shorter latency than reported for eclosion hormone. For example, the latency between hormone application and emergence of the behavior is very short, from 2 to 10 min, while eclosion hormone application is followed by latencies of 15 min to 3 hours, depending on the stage of development (Truman, 1978; Weeks and Truman, 1984a, 1984b; Miles and Weeks, (1991). The isolated central nervous system responds to ETH, but not to eclosion hormone, with patterned motor bursting corresponding to in vivo pre-ecdysis and ecdysis. Another distinguishing characteristic between ETH and eclosion hormone lies in the observation that eclosion hormone acts to promote release of ecdysis triggering hormone. While not intending to be limited to any particular mechanism of action, ETH may be an immediate blood-borne trigger for ecdysis through a direct action on the nervous system. Yet another distinguishing characteristic lies in the window of ecdysis sensitivity between ETH and eclosion hormone, ecdysis promoting sensitivity to ETH existing much earlier than for eclosion hormone.

These observations support the role of ETH as an immediate trigger for pre-ecdysis and ecdysis, and the independent identity of these peptides and proteins in developments apart from other families of peptides and proteins previously described.

In certain embodiments, the invention concerns isolated nucleic acid molecules, DNA segments and recombinant vectors which encode an ecdysis triggering hormone or the ETH-PRP1 or ETH-PRP2, that includes an amino acid sequence essentially as set forth in SEQ ID NO:1, 2, 3, 13, 14, or 15. The term "a sequence essentially as set forth in SEQ ID NO:1, 2, 3, 13, 14, or 15" for example, means that the sequence substantially corresponds to a portion of SEQ ID NO:1, 2, 3, 13, 14, or 15, and has relatively few amino acids which are not identical to, or a biologically functional equivalent of, the amino acids of the indicated SEQ ID NO:1, 2, 3, 13, 14 or 15 sequence.

The term "biologically functional equivalent" is well understood in the art and is further defined in detail herein. For example, biologically functional equivalents of ETH are intended to embrace peptide, protein, or other organic molecules that include an amino acid sequence that encode a molecule of the forms noted which are capable of initiating early or enhancing the initiation of pre-ecdysis behaviors or ecdysis triggering hormone activity as described here, either alone or in combination with one another. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:1, 2, 3, 13, 14, or 15 will be sequences which are "essentially as set forth "in SEQ ID NO:1, 2, 3, 13, 14, or 15".

In certain other embodiments, the invention concerns isolated DNA segments and recombinant vectors that include within their sequence a nucleic acid sequence essentially as set forth in SEQ ID NO:4, 16, 17, 18, 19, 20, 21, 22, 23, 24, or 25". The term "essentially as set forth in SEQ ID NO:" is used in the same sense as described above and means that the nucleic acid sequence substantially corresponds to a portion of SEQ ID NO:4, 16, 17, 18, 19, 20, 21, 22, 23, 24, or 25, and has relatively few codons which are not identical, or functionally equivalent, to the codons of the indicated sequence ID number.

As is known in the art, codons are groups of three nucleotides which, in the terms of the coding exons, encode a particular amino acid. The term "functionally equivalent codon" is used herein to refer to codons that encode the same amino acid, such as the six codons for arginine or serine, and also refers to codons that encode biologically equivalent amino acids.

It will also be understood that amino acid and nucleic acid sequences may include additional residues, such as additional N-or C-terminal amino acids, and yet still be essentially as set forth in one of the sequences disclosed herein, so long as the sequence meets the criteria set forth above. This particularly applies to nucleic acid sequences which may, for example, include various non--coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 60% and about 99%; or more preferably, between about 75% and about 99%; or even more preferably, between about 8% and about 99%; of nucleotides which are identical to the nucleotides of SEQ ID NO:4, 16, 17, 18, or 19 will be sequences which are "essentially as set forth in SEQ ID NO:4, 16, 17, 18, or 19". Sequences which are essentially the same as those set forth in SEQ ID NO:4, 16, 17, 18, or 19, may also be functionally defined as sequences which are capable of hybridizing to a nucleic acid segment containing the complement of SEQ ID NO:4, 16, 17, 18 or 19 under relatively stringent conditions. Suitable relatively stringent hybridization conditions will be well known to those of skill in the art and are clearly set forth herein, for example see example 9, which describe conditions such as.

Following conventional designation of amino acid and nucleic acid terminology, the following letter designations will be employed in the description of the amino acid embodiments of the present invention:

Alanine=Ala (A); Arginine=Arg (R); Aspartate=Asp (D);

Asparagine=Asn (N); Cysteine=Cys (C); Glutamate=Glu (E);

Glutamine=Gln (Q); Glycine=Gly (G); Histidine=His (H);

Isoleucine=Ile (I); Leucine=Leu (L); Lysine=Lys (K);

Methionine=Met (M); Phenylalanine=Phe (F); Proline=Pro (P);

Serine=Ser (S); Threonine=Thr (T); Tryptophan=Trp (W);

Tyrosine=Tyr (Y); Valine=Val (V).

Table 1 lists the identity of sequences of the present disclosure having sequence identifiers.

TABLE 1

Identification of Sequences Having Sequence Identifiers

| SEQ ID NO: | IDENTITY |
|---|---|
| 1 | Thr—Asn—Lys—Asn—Ile—Pro—Arg—Met, an octomer of ETH |
| 2 | SNEAFDEDVMGYVIKSNKNIPRM, ETH from *Bombyx mori* |
| 3 | SNEAISPFDQGMMGYVIKTNKNIPRM, ETH from *Manduca sexta* |
| 4 | Nucleic acid sequence encoding SEQ ID NO:1 (octomer) |
| 5 | 5'-GACTCGAGTCGACATCGA(T)$_{17}$,adaptor-oligo (dT) primer for RACE |
| 6 | 5'-GACTCGAGTCGACATCG, adaptor primer sequence for RACE |
| 7 | 5'-TTCGA(TC)CA(AG)GG(N)ATGATGGG, 3'-GSP1 primer sequence |
| 8 | 5'-GTCAT(ATC)AA(AG)ACIAA(TC)AA(AG)AA, 3'-GSP2 primer sequence |
| 9 | 5'-CGGCTGTGCGTCATCTTCATATAG, 5'-GSA0eprimer sequence |
| 10 | 5'-CCATGGGTAAAGCTTTGGAATATC, 5'-GSP2 primer sequence |
| 11 | 5'-GTTAGGTGTTCCCGCGTAAACTAG, forward primer sequence for PCR of ETH gene |
| 12 | 5'-AATGACTAGAAATTATTTAAGTACAGG, reverse primer sequence for PCR of ETH gene |
| 13 | amino acid sequence of ETH precursor related peptide 2 |
| 14 | amino acid sequence of ETH precursor related peptide 1 |
| 15 | amino acid sequence encoded by precursor cDNA |
| 16 | nucleotide sequence of precursor cDNA |
| 17 | nucleotide sequence encoding ETH-precursor related peptide 2 |
| 18 | nucleotide sequence encoding ETH from *Manduca sexta* |
| 19 | nucleotide sequence encoding ETH precursor related peptide 1 (ETH-PRP1) |
| 20 | antisense full length cDNA (leading sequences and poly-A included) ETH precursor |
| 21 | antisense - cDNA ETH precursor |
| 22 | antisense - nucleic acid sequence ETH |
| 23 | antisense - nucleic acid sequence ETH-PRP1 |
| 24 | antisense - nucleic acid sequence ETH-PRP2 |
| 25 | ATGTACAAGCTCACAGTCTTCCTGATGTTCATCGCTTTCGTCATAATCGCT GAAGCCTCAAACGAAGCAATATCGCCATTCGACAAGGCATGATGGGATACG TTATTAAAACAAACAAAAACATTCCAAGAATGGGCTAATAG*synthetic gene for Mas-ETH with an adipokinetic hormone signal sequence |

Other applications of ETH exist in urban and dwelling settings, for the control of pests of domestic animals and household insects, such as fleas, termites, mosquitos and biting flies, cockroaches, tapeworms, hookworm and termites.

Following long-standing patent law convention, the terms "a" and "an" mean "one or more" when used in this application, including the claims. The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

EXTRACTION OF ETH AND GENE RELATED PEPTIDES FROM ENDOCRINE OR NEUROENDOCRINE TISSUE GLANDS

The present example outlines a particular technique that was used in the isolation of the ETH hormone from insect preparations.

ETH was extracted from the endocrine glands of *Manduca sexta* in the present example, and as particularly present in Inka cells. However, those skilled in the art will appreciate that ETH may be obtained from neuroendocrine or endocrine tissues of any variety of non-lepidopteran pest insects, including:

Coleoptera (colorado potato beetle, *Leptinotarsa decimlineata*; corn rootworm (*Helicoverpa zea*).

Hemiptera (Lygus bugs)

Homoptera (beet leafhopper)

Diptera (mosquitos, biting flies)

Orthoptera (cockroaches, *Periplaneta americana, Blattella germanica, Blatta orientalis*)

In some of the following studies, the present inventors extracted, EG of pharate pupae of *Manduca sexta* in physiological saline, and injected the extract into the hemocoel of pharate larvae, pupae, and adults at various times prior to normal ecdysis. In other studies, the ETH and related peptides were purified extracted peptides reconstituted in a suitable injectable carrier.

PREPARATION OF ETH EXTRACT

Epitracheal glands were dissected into a microtissue grinder and kept on dry ice until extraction into Weever's saline. Extracted samples were heated in a 90° C. water bath for 2 to 3 min., cooled on ice, centrifuged at 10,000 g and the supernatant was injected directly into the hemocoel. EG extracts triggered ecdysis within minutes of injection at all stages.

A peptide with ecdysis-triggering activity was also purified from an extract of 50 pharate pupal EG with reversed-phase liquid chromatography (RPLC) (FIG. 1A). For HPLC fractionation, freshly-dissected EG were homogenized in acidic methanol (MeOH: $H_2O$:acetic acid, 90:9:1) and the supernatant was evaporated to dryness. Crude extracts of EG were fractionated with a Microsorb C4 column (wide pore 300 A, 4.6 mm/25 cm), with a linearly increasing gradient of acetonitrile (3 to 53% in 90 min) in constant 0.1% TFA/water using a flow rate of 1 ml/min. Fractions were collected based on UV absorbance (220 nm) and vacuum centrifuged to dryness. Individual fractions were re-suspended in physiological saline and injected into pharate fifth instar *Manduca sexta* larvae. Induction of preecdysis behavior, visible as synchronous dorso-ventral contractions in body segments, were scored as positive responses. MasETH was found to elute at 55 min under the conditions described above, and was 95% pure after a single fractionation step.

Liquid secondary ion mass spectrometry (LSIMS) showed the peptide to have a molecular mass of $2940.5 \pm 0.1$ Da. LSIMS was carried out using a JEOL JMS HX110 mass spectrometer fitted with a Cs+ ion gun. An electric field scan was employed across a narrow mass range, using mass calibration with clusters of $(CsI)_n$ Cs±. The monoisotopic mass (MH+) for native MasETH was measured at $2940.5 \pm 0.1$ amu. This indicates that the peptide contains a COOH-terminal amide group (theoretical MH+ of 2940.45 for the aminated peptide, $2941.44 \pm 0.98$ for the free carboxyl).

Figure 1B:
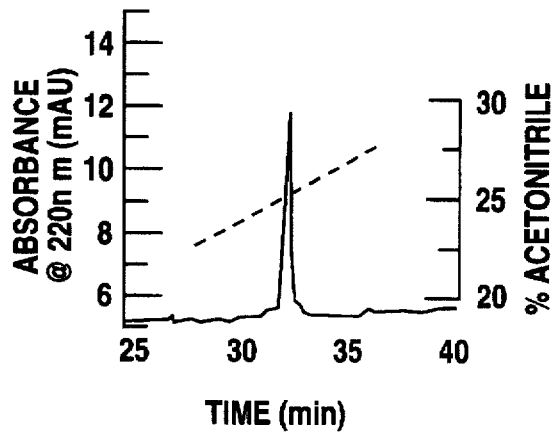
Figure 1C:
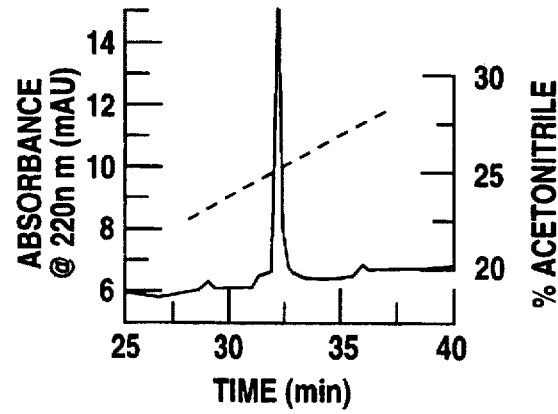

Edman microsequencing revealed a polypeptide of 26 amino acids with the sequence shown in SEQ ID NO:3. Automated. Edman degradation sequencing was performed with an Applied Biosystems 475A pulsed-liquid sequenator coupled on-line with an ABI 120A analyzer for identification of PTH-derivatized amino acids. The COOH-terminal amidation indicated by the predicted mass of 2940.45, (calculated mass of the free acid is 2941.44) was confirmed by chemical synthesis. This peptide was named *Manduca sexta* ecdysis triggering hormone 1, or Mas-ETH. Synthetic Mas-ETH has a molecular mass of $2940.4 \pm 0.1$ (as determined by LSIMS described above) and co-elutes with the native peptide under a variety of RPLC conditions (FIGS. 1B and 1C).

On the basis of RPLC peak integrations and quantative amino acid composition analyses, each pharate pupal Inka cell was estimated as containing approximately 10 pmol of Mas-ETH 3 to 4 hr prior to natural pre-ecdysis. To quantify levels of Mas-ETH in EGs, peak integrations from RPLC were related to molar quantities obtained from quantitative amino acid composition analysis.

Peptide samples (1 nmol) were hydrolyzed with HCl vapor at 150° C. for 90 min, and analyzed with an Applied Biosystems model 420 microamino acid analyzer. Molar quantities of PTC amino acids were determined by peak integration and corrected against a 500 pmol norleucine standard.

Animals were staged 3 to 4 hours prior to natural ecdysis by observation of the morphological marker, anterior shrink, as defined by Truman, et al., (1980). With 18 Inka cells per animal, it was estimated that there is a total of 180 pmol of MasETH per individual. If the blood volume of a pharate pupa is 1.0 ml, release of the entire complement of Inka cells could generate a physiological concentration of 180 nM.

A relatively small COOH-terminal amino acid sequence of MasETH, Pro-Arg-Met-$NH_2$, was found to be identical to that of $SCP_B$ (Morris et al., 1982) and may explain the $SCP_B$-like immunoreactivity of the Inka cells. While not intending to be limited to any theory, MasETH in the EG is probably produced primarily by the Inka cells. This is postulated because $SCP_B$-like immunoreactivity was found by the present inventors to be limited to the Inka cells and because extracts of pharate adult EG, which consist of a single Inka cell, show potent ecdysis-triggering activity.

Mas-ETH-like biological activity was detected in the hemolymph during pre-ecdysis of both pharate 5th instar larvae and pharate pupae. Hemolymph was collected and fractionated by RPLC just after the onset of pre-ecdysis in both stages. Biological activity, measured as ability to induce pre-ecdysis and ecdysis, co-eluted with Mas-ETH in both instances. The purified fraction obtained from pharate pupae during pre-ecdysis was subjected to electrospray mass spectrometry and has a molecular mass of $2945 \pm 2$, a value close to that of Mas-ETH.

Hemolymph samples were obtained from pharate fifth instar larvae by cutting the posterior horn. For pharate pupae, a lateral incision was made on the dorsal side of the 4th abdominal segment. Hemolymph was collected into acidified methanol. The samples were centrifuged in a Beckman J2-21 centrifuge using a JA-20 fixed-angle rotor for 30 min at 9500 rpm and 4° C. The supernatant was dried by vacuum centrifugation. Samples were de-salted with Sep-pak $C_{18}$ cartridges prior to fractionation. For electrospray mass spectrometry analysis, fractions were vacuum evaporated and re-solved in methanol:water (50:50). Mass analysis was performed with a Finnigan-MAT high resolution mass spectrometer fitted with a electrospray interface operated in positive ion mode.

In control studies when hemolymph was collected 8 hours prior to ecdysis in larvae and 3.5 hours prior to ecdysis in pupae, no Mas-ETH-like biological activity was detected. Thus, Mas-ETH appears in the hemolymph at the appropriate time to trigger ecdysis.

The following table provides an exemplary list of the lepidopterous insects from which the described EHT-1 peptide hormone may be extracted.

TABLE 2

*Manduca sexta*

*Bombyx mori*

*Helicthis virescens*

Insects of the order Coleoptera that includes beetles, as well as insects such as flies, cockroaches (*Periplaneta americana*), and grasshoppers, are expected to be sensitive to an ecdysis triggering hormone similar to the hormone provided by the present invention. In particular, the tobacco hornworm, the army worm, diamond back moth, common white, tobacco cutworm, oriental fruit moth, peach leaf miner, and rice stem borer, as well as like insects, are expected to be sensitive to the developmental effects of ETH, as well as sources of ETH.

Saline and methanol were used in the particular extraction protocols outlined in the present example. However, other medium may also be used to obtain ETH as recognized by those of ordinary skill in the art.

EXAMPLE 2

IN VITRO ACTIVITY OF ETH ON THE CENTRAL NERVOUS SYSTEM

Application of Mas-ETH to the isolated Larval or pupal central nervous system in vitro elicited motor burst patterns that clearly correspond to natural pre-ecdysis and ecdysis behaviors.

To demonstrate the above phenomenon, the entire central nervous system was removed from the animal and suction electrodes were used to record bursting activity in dorsal nerves of abdominal ganglia from segments 5–7 (A5, A6, A7). The entire central nervous system or a chain of abdominal ganglia dissected from pharate fifth instar larvae or pharate pupae were placed in a 300 ml Sylgard bath and bathed in modified Weever's saline. Motor output was recorded extracellularly from dorsal roots of abdominal ganglia A5, A6, and A7 using polyethylene suction electrodes. Potentials were amplified with Grass P-15 AC amplifiers, captured on video tape, and played back on a Gould Brush pen recorder. To record natural pre-ecdysis and ecdtysis, the nervous system was removed after initiation of the behavior.

For studies involving bath application of synthetic MasETH, pharate 5th instar nerve cords were dissected at −8 hr prior to ecdysis, using liquid-Lilled head and brown mandibles as morphological markers. Pharate pupae were dissected at 8 hours prior to natural ecdysis using brown bars as the morphological marker.

The tracheal system was removed in all studies. The pattern of pre-eccdysis in isolated pharate 5th instar CNS under natural conditions was quite similar to that elicited by application of 100 nM Mas-ETH. To observe natural pre-ecdysis and ecdysis motor patterns, animals were observed until initiation of pre-ecdysis, at which time nerve cords were quickly removed and prepared for suction electrode recordings. In both instances, pre-ecdysis bursts occurred synchronously in the dorsal nerves of A5–A7 every 10 to 12 seconds with a duration of 5 to 10 sec. Similarly, the burst pattern driving ecdysis in pharate larvae under natural conditions was similar to that resulting from exposure to 1 mM Mas-ETH. Ecdysis bursts occurred every 20 to 30 seconds and were about 20 sec in duration, with an intersegmental delay of about 5 sec. Burst durations and intervals between bursts became longer as the behavior progressed, which corresponded to observations of natural behavior patterns. Optimal Mas-ETH concentrations for triggering pre-ecdysis were lower than those necessary for ecdysis.

Concentrations of Mas-ETH necessary to elicit ecdysis motor patterns from pharate pupal nerve cords were higher, in the 1 uM to 5 uM range. These differences may reflect a requirement for additional components in the EG that act in concert with MasETH. Indeed, the present inventors initial RPLC data show that the EG produce at least two additional peptides with ETH-like biological activity, the ETH-PRP1 and ETH-PRP2.

The isolated central nervous system can generate pre-ecdysis and ecdysis motor patterns following Mas-ETH treatment in the absence of the tracheal system. These data contrast with earlier reports that eclosion hormone (that is, extracts of the adult corpora cardiaca, Truman, 1978; Weeks and Truman, 1984a, 1984b; Miles and Weeks, 1991) does not elicit ecdysis from isolated nerve cords unless the tracheal system and its attachments to the spiracles are intact.

It is interesting to note that the EG are attached to the outer wall of tracheal tubes near each segmental spiracle. The requirement of the tracheal system for eclosion hormone action therefore may relate to the presence of the EG rather than the presumed role of the tracheal system in oxygenation of the nervous system. The present inventors have also found that corpora cardiaca extracts (an eclosion hormone preparation, Thurman, 1978) are ineffective in evoking pre-ecdysis and ecdysis in isolated nerve cords lacking the tracheal system (5 studies). However, some of the present inventors studies showed that corpora cardiaca extracts were effective in triggering pre-ecdysis and ecdysis bursting patterns in the presence of freshly-dissected pharate pupal epitracheal glands (3 out of 3 studies).

EXAMPLE 3

INDUCTION OF ECDYSIS IN VIVO; 5TH INSTAR LARVAE WITH ETH COMPARATIVE SENSITIVITY WITH ECLOSION HORMONE

The present example demonstrates the utility of the present invention for promoting early ecdysis in an invertebrate animal, such as in insects. Such provides an effective technique for controlling insect and other pests. The present example also demonstrates one of the distinguishing biological activities between ETH and eclosion hormone. Specifically, while the isolated central nervous system responded to ETH, it did not respond to eclosion hormone, with the patterned motor bursting demonstrated with ETH corresponding to in vivo pre-ecdysis and ecdysis. In addition, the developmental window of sensitivity to ETH is demonstrated to be much broader than sensitivity to eclosion hormone as compared to eclosion hormone.

Natural ecdysis in pharate 5th instar larvae is preceded by a well-defined pre-ecdysis behavior, characterized by dorso-ventral contractions that occur synchronously in abdominal and thoracic segments (Copenhaver and Truman, 1982; Truman and Weeks, 1983, 1985). Contractions, visible as a dimpling of the dorso-lateral body wall, begin in the most posterior segment, and gradually spread anteriorly. Pre-ecdysis behavior typically lasts 60 to 80 min, and is followed by ecdysis behavior, which lasts about 10 min. Ecdysis behavior is characterized by a distinctly different motor pattern consisting of peristaltic waves of contractions, which originate in the most posterior segment and move anteriorly (Weeks and Truman, 1984). Using a pressure transducer to record changes in internal pressure, in vivo measurements of pre-ecdysis and ecdysis contraction patterns were obtained in pharate 5th instar larvae and pharate pupae. Internal hydrostatic pressure was measured in pharate 5th instar larvae and pharate pupae of *Manduca sexta* with a Gould-Statham P23-ID pressure transducer. The transducer was connected to a saline-filled tube which in turn was attached to the posterior dorsal horn of pharate 5th instar larvae and pharate pupae with low melting point dental wax.

Pharate is the term used to describe animals which have synthesized a new cuticular layer, yet remain encased in the old cuticle; this stage ends after ecdysis is completed.

Figure 2A:
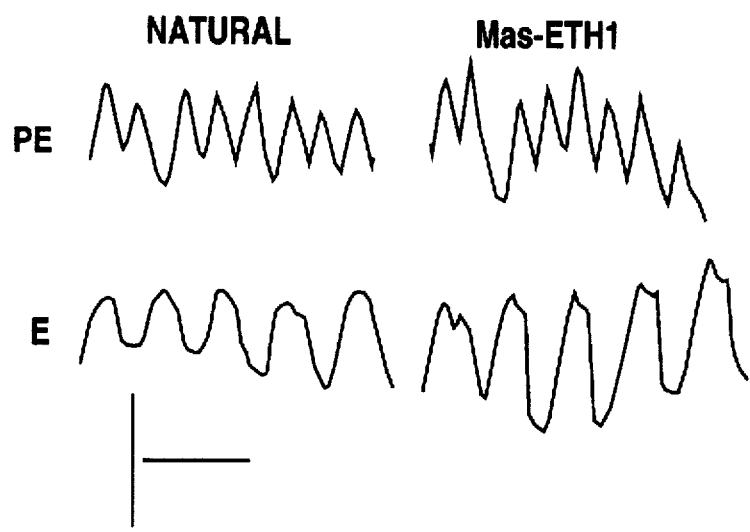

During natural pre-ecdysis in the larva, dorso-ventral contractions typically occur every 10 to 12 seconds with a duration of 5 to 7 seconds (FIG. 2A). When pharate larvae were injected with Mas-ETH (20 pmol to 1 nmol), pre-ecdysis began within 2 to 10 min, and the pattern was indistinguishable from that observed under natural conditions (n=13). The pre-ecdysis induced by Mas-ETH injection lasted 35 to 65 min, and was followed by ecdysis (FIG. 2A). Depending on the stage of injected larva, ecdysis behavior lasted from 10 min to 2 hours.

Fifth-instar larvae respond to Mas-ETH injection up to 36 hours prior to normal ecdysis by exhibiting pre-ecdysis behavior within 6 to 10 min (n=7). If injected at the time of head capsule slip some 2 hours later (34 hours prior to normal ecdysis), larvae exhibit both pre-ecdysis and ecdysis motor patterns. At about 36 hours preceding natural ecdysis in pharate 5th instar larvae, the first signs of apolysis can be observed as an accumulation of molting fluid in the prothorax. About two hours later, head capsule slip occurs (Curtis et al., 1984). Premature ecdysis behavior induced by Mas-ETH injection (34–10 hours prior to natural ecdysis) lasted from 10 to 45 min. In these instances, ecdysis could not be completed and motor activity ceased. Mas-ETH triggered successful ecdysis only after the old cuticle is sufficiently digested, some 6 to 8 hr before normal ecdysis. Sensitivity to ETH, therefore, is shown to exist during the pharate stage.

The pharate stage is generally described as beginning with head capsule slip and ending with the insect breaking out of the old cuticle, about a 48 hour period under the described conditions.

The early onset of Mas-ETH sensitivity (1 to 2 days prior to normal ecdysis) contrasts with the relatively narrow period of responsiveness to eclosion hormone near the end of each molt (Reynolds et al., 1979; Copenhaver and Truman, 1982; Truman et al., 1980; Truman, 1992). Pharate larvae injected with eclosion hormone 6 to 12 hours prior to normal ecdysis show only pre-ecdysis behavior. Sensitivity for both pre-ecdysis and ecdysis behaviors begins just 6 hours before normal ecdysis. If eclosion hormone is injected at the beginning of the sensitive period, the delay from injection to appearance of both behaviors is about 3 hours.

EXAMPLE 4

ECDYSIS INDUCTION IN PHARATE PUPAE AND ADULTS WITH ETH

The present example is provided to demonstrate the activity of the present ETH peptides, proteins, and homologs thereof, in inducing ecdysis in insects that are at a later stage of development and as adults.

Figure 2B:
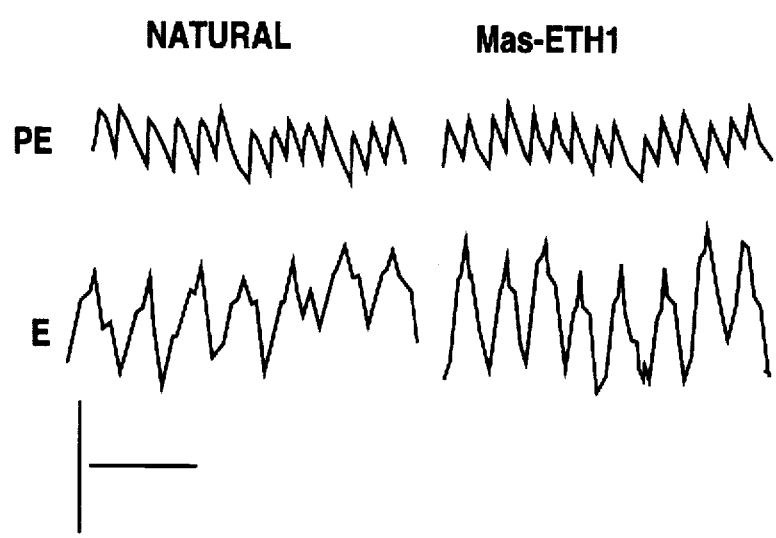
Figure 3A:
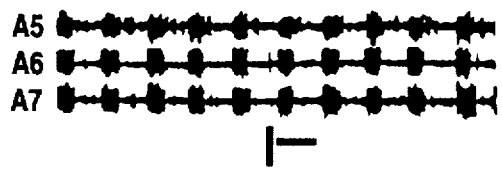
Figure 3B:
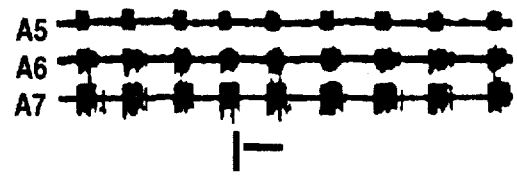
Figure 3C:
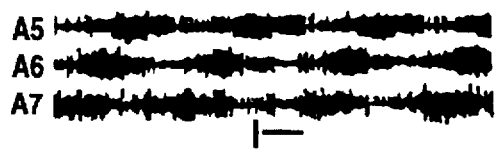
Figure 3D:
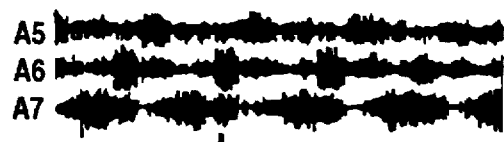
Figure 3E:
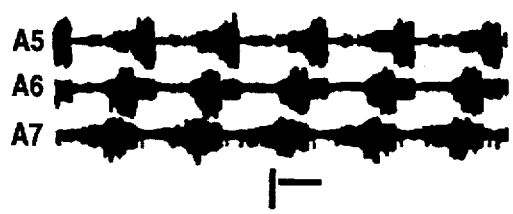
Figure 3F:
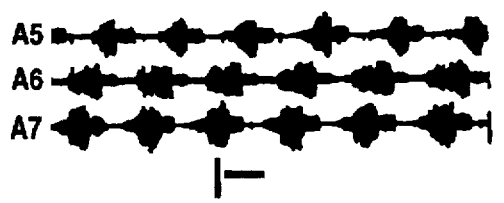

The present study demonstrates the utility of ETH, in the form of Mas-ETH injections, for triggering ecdysis in pharate pupae and adults. Pharate pupae responded to injections (400 pmol to 1 nmol) (FIG. 2B; n=12) up to 48 hours prior to natural ecdysis. Although pre-ecdysis of pharate pupae at these earlier stages of development was difficult to discern visually, blood pressure measurements revealed a clear rhythm within minutes of Mas-ETH injection (FIG. 2B). Ecdysis followed after a period of 50 to 90 min. Pharate adults responded to Mas-ETH injections (1 to 2 nmol) up to 24 hours prior to natural ecdysis (n=10). Rotatory movements of the abdomen began within 3 to 10 min of injection and were followed by a period of relative quiescence. Adults emerged 2 to 3 hours later, before resorption of molting fluid, and hence were wet and could not inflate their wings.

As demonstrated in the prior example, in pharate pupae, responsiveness to eclosion hormone begins at about 8 hours prior to ecdysis, and the delay between injection at this time and onset of behavior is 140 min. Pharate adults show only a 4 hour window of sensitivity to eclosion hormone (Reynolds et al., 1979; Copenhaver and Truman, 1982; Truman et al., 1980; Truman, 1992). The present inventors results with Mas-ETH show that the motor program driving pre-ecdysis and ecdysis in all life stages is already fully competent at developmental stages far earlier than the appearance of sensitivity to the eclosion hormone. Furthermore, the latency to the onset of Mas-ETH effects is invariably short, ranging from 2 to 10 min. It follows that the late-emerging sensitivity to eclosion hormone depends on events other than behavioral competence, perhaps an onset in the ability of epitracheal glands to release Mas-ETH.

EXAMPLE 5

IMMUNOHISTOCHEMISTRY OF *M. SEXTA* ENDOCRINE SYSTEM

While investigating immunohistochemical staining patterns prior to and after ecdysis, the present inventors observed a segmentally distributed system of paired epitracheal glands (EGs) in larvae, pupae and adults of *M. sexta*. Endocrine glands homologous to the EG were described previously in the waxmoth *Galleria mellonella* during a search for organs containing FMRFamide-like peptides (Zitnan, D., 1989).

Longitudinal sections of whole pharate and freshly ecdysed larvae, pupae and adults were stained with an antiserum to FMRFamide. Intense staining was observed in large, segmentally distributed cells located near each spiracle in pharate stages; staining was not detected in freshly ecdysed animals, suggesting that some components of these cells may control processes associated with ecdysis. Zitnan (1989) originally referred to the Galleria structures as perispiracular glands. However, since Keilin (1944) had used the term perispiracular glands to describe a different anatomical structure, the present inventors have chosen here the name epitracheal glands for the structures in *Manduca sexta*, in order to indicate their proximity to each spiracle.

Each animal contains 18 EGs; individual EGs, which are quite variable in size and shape, are attached to the ventral surface of the major ventro-lateral tracheal tube near each spiracle. The most prominent component of the EG is a large white Inka cell, which increases in volume and opacity as ecdysis approaches and can reach diameters of 250 mm. Nuclear staining with DAPI and immunohistochemical staining with antibodies to horseradish peroxidase and molluscan small cardioactive peptide B (SCP$_B$) revealed that, in addition to the peptidergic Inka cell, each EG consists of 2 to 3 smaller glandular cells of unknown function. In most cases, all cells of the EG are observed in a single bundle, but occasionally the Inka cell is separated from the other gland cells. Trachei with attached EG were dissected under saline and fixed in Bouin's fixative, washed in 70% ethanol and phosphate-buffered saline with 0.5% Triton X-100 (PBST), and incubated with fluorescein-labelled anti-horseradish peroxidase (January and January 1982). Tissue was washed and mounted in glycerol with diphenylenediamine (antifade) and the nuclear dye DAPI (4',6-diamidino-2-phenyl-indole; 1 to 2 mg/ml). Preparations were observed under a fluorescent microscope using a triple band pass filter (for Fluorescein, Texas Red and DAPI) and UV filter (for DAPI only). For immunohistochemical staining with a monoclonal antibody to SCP$_B$ staining (Masinovsky, et al., 1988), paraffin sections of EG were prepared as described by Zitnan (1993). Tissues were fixed in Bouin's fixative, dehydrated in ethanol and chloroform and embedded in Paraplast. Rehydrated sections 10 to 15 mm thick were incubated overnight with the monoclonal antibody to SCP$_B$, rinsed and incubated with a peroxidase-labelled anti-mouse IgG (Vector Laboratories, Burlingame, Calif.) for 1 hour and bound peroxidase was stained with 3-amino-9-ethyl carbazole (Sigma, St. Louis, Mo.).

Pharate is the term used to describe animals which have synthesized a new cuticular layer, yet remain encased in the old cuticle; this stage ends after ecdysis is completed. In the pharate adult stage, the Inka cell is alone, because the neighboring gland cells have been lost during metamorphosis. After ecdysis, Inka cells are reduced in volume and have lost their white appearance. At this time, SCP$_B$-like immunoreactivity also disappears. These observations suggest that the endocrine contents of Inka cells are released during ecdysis.

EXAMPLE 6

ORALLY ACTIVE INSECTICIDAL PREPARATIONS

The various peptides/proteins of the present invention may be formulated within liposomes. Liposomal incorporation of peptides/proteins is a technique well known to those of skill in the art, and has been used in the liposomal preparations of insulin. These techniques are specifically incorporated herein by reference for this purpose, and may be used to evaluate ETH, ETH precursor, ETH-PRP1, ETH-PRP2, or a combination thereof in liposomes such formulations as expected to render these preparations orally active upon ingestion by insects, hence providing an additional delivery technique.

EXAMPLE 7

SYNTHETIC PREPARATIONS OF ETH

Synthetic MasETH was prepared using standard solid state synthesis using an automated peptide synthesizer, employing standard t-BOC chemistry. For this study, the amidated 26 mer having the sequence defined in SEQ ID NO:3 was synthesized on an Applied Biosystems automated peptide synthesizer located at the Peptide Synthesis Facility at the Sussex Center for Neuroscience, University of Sussex, Brighton, UK.

Solid state peptide synthesis is well known to those of ordinary skill in the art, and is described generally by Merrifield, which is specifically incorporated herein by reference. The peptides and proteins disclosed herein may thus be prepared using these relatively routine techniques given the disclosure of the present invention.

Synthetic Mas-ETH was prepared using standard solid state synthesis using Fmoc chemistry. In the present studies, the amidated 26 mer having the sequence defined in SEQ ID NO:3 was synthesized on a Porton automated peptide synthesizer located at the Peptide Synthesis Facility at the Sussex Center for Neuroscience, University of Sussex, Brighton, UK.

Synthesis is accomplished by solid phase peptide synthesis using the Fmoc strategy using an automated peptide synthesizer. This method involves building an amino acid chain from the —COOH terminus, which is attached to an insoluble polymeric support. The base-labile Fmoc group is used to protect the -amino group of each residue. Residues having potentially reactive side chains are protected with acid-labile groups such as t-butyl. After removal of the Fmoc group during each cycle with piperidine, the next protected amino acid is added using either a coupling reagent or pre-activated amino acid derivative. At the end of the synthesis, the peptide is cleaved from the solid support to yield a peptide acid or amide, depending on the linking agent used, and the side-chain protecting groups are removed by treating the peptide-resin with a mixture of trifluoroacetic acid and various ion scavengers. Methyl t-butyl ether is added to precipitate the peptide out of the cleavage mixture. The crude peptide is dissolved and lyophilized, after which it was purified by high performance liquid chromatography. The purified peptide is lyophilised and stored at –80° C.

Solid state peptide synthesis is well known to those of ordinary skill in the art, as described by the references provided (Atherton and Sheppard, 1989; Fields and Noble, 1990). The peptides and proteins disclosed herein may thus be prepared using these relatively routine techniques given the disclosure of the present invention.

EXAMPLE 8

VIRAL CONSTRUCTS FOR DELIVERY OF ETH, OR ETH-RELATED GENES INTO PEST INSECTS

Sequences of Mas-ETH clones used to make viral constructs are provided in the present example. The viral construct used for Mas-ETH alone was: (synthetic gene with adipokinetic hormone signal sequence; see Bradfield and Keeley, 1989 for background on AKH signal sequence).

ATGTACAAGCTCACAGTCTTCCTGATGTTCATCGCTTTC GTCATAATCGCT
GAAGCCTCAAACGAAGCAATATCGCCATTCGACAAGGCATGATGGGATACG
TTATTAAAACAAACAAAAACATTCCAAGAATGGGCTAATAG (SEQ ID NO: 25)

A viral construct was also prepared and used to express ETH and the ETH-PRP1 and ETH-PRP2 nucleic acid sequences (SEQ ID NO:19 and SEQ ID NO:17, respectively). The particular sequence used was the same as SEQ ID NO:16 in Table 1.

ATGGCCTTTAGGGTAACTAAGGTATTAACGGCGTTGTGCCTAGTATGTTTATTTTTGCAA
GTGGAAAGTTCATTTATTAAGCCAAATAATGTACCGAGGGTAGGCAGAAGCAATGAAGCT
ATTAGCCCATTCGATCAAGGAATGATGGGGTATGTGATTAAAACTAATAAAAATATACCA
CGCATGGGAAGAAGAAACTATGATTCGGAAAATCGTTTCGATATTCCAAAGCTTTACCCA
TGGCGTGCCGAAAATACAGAACTATATGAAGATGACGCACAGCCGACAAATGGTGAAGAA
ATCAATGGTTTCTATGGGAAACAACGAGAAAATATGAAACGATGA

Both of these DNAs were cloned into the Bg1II-EcoRI sites of the baculoviral vector pACUW21. These baculoviral vectors will be used in insecticidal preparations in controlling insects.

In the preparation of viral constructs for delivery of ETH or ETH-related genes to insects generally, a synthetic gene encoding ETH or alternatively, its cDNA precursor, will be incorporated into a suitable baculovirus (example: AcNPV; *Autographa californica* nuclear polyhedrosis virus). The coding region of ETH or its precursor will be flanked at the 3' end by an appropriate signal sequence (e.g., the adipokinetic hormone signal described in Bradfield and Keeley (1989) and at the 5' end by an appropriate stop codon (e.g., TAA). The expression of the hormone coding sequences will be under the control of appropriate promoters such as "p10," "polyhedrin," or "basic protein." Constructs will be ligated into suitable vector elements, such as pACUW21 for a single promoter construct or pACUW51 for multiple promoter constructs (detailed descriptions of various type of viruses, constructs, and vectors are found in O'Reilley, et al. (1992)).

EXAMPLE 9

CLONING OF THE CDNA PRECURSOR

The present example outlines one method for cloning the ETH gene.

A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule. Techniques such as these would also, of course, be appropriate for the production of an EHT in accordance with the present invention.

The first step in such cloning procedures is the screening of an appropriate DNA library, such as, in the present case, a DNA library prepared from endocrine and/or neuroendocrine tissue of an insect, such as lepidopterous insects. The screening procedure may be an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. After identifying an appropriate DNA molecule, it may be inserted into any one of the many vectors currently known in the art and transferred to a prokaryotic or eukaryotic host cell where it will direct the expression and production of the so-called recombinant version of the protein.

It will be understood that recombinant ETH may differ from naturally-produced ETH in certain ways. In particular, the degree of post-transnational modifications, such as, for example, glycosylation and phosphorylation may be different between the recombinant ETH and the ETH purified from a natural source, such as the lepidopteran insect, the hornworm.

MATERIALS AND METHODS

RNA isolation. mRNA was extracted from 75 perispiracular glands (PSG) from *M. sexta*. The cells were suspended in 100 ml lysis/binding buffer (100 mM Tris-HCl, pH 8.0, 500 mM LiCl, 10mMEDTA, pH 8.0, 1% LiDS, 5 mM dithiothreitol) and were pipetted several times in order to lyse them. Solid material was spun down and the supernatant was transferred to a fresh tube containing 10 ml Dynabeads (magnetic beads covalently bound to oligo(dT) tails). MRNA was purified according to the manufacturers' directions (Dynal) and left immobilized on the Dynabeads.

Solid Phase 1st Strand cDNA Library Construction. After several washes in Reverse Transcriptase(RT) reaction buffer, (20 mM Tris-HCl, pH 8.4, 50 mM KCl), the beads with the attached mRNA were resuspended in RT reaction buffer, heated to 70° C. for 10 minutes and kept on ice while being supplemented with 2.5 mM $MgCl_2$, 1 mM dNTPs, and 10 mM DTT. In order to perform $1^{st}$ strand cDNA synthesis using the oligo(dT) tails as primer, the beads with attached mRNA were incubated at 42° C. for 10 minutes before the addition of one unit of Superscript reverse transcriptase enzyme (GIBCO BRL Life Technologies, Gaithersburg, Md.), after which, they were incubated at 42° C. for 50 minutes followed by enzyme inactivation at 70° C. for 15 minutes. The solid phase library was resuspended in TE (10 mM Tris-HCl, pH 8.0, 1 mM EDTA) and the mRNA was released from the cDNA/mRNA hybrid by heating the library to 95° C. for one minute and immediately separating the liquid phase (containing the mRNA) from the beads (containing the immobilized $1^{st}$ strand cDNA).

3' RACE. The beads with attached $1^{st}$ strand cDNA were washed with 1×PCR (polymerase chain reaction) buffer (20 mM Tris-HCl, pH 8.4, 5 mM KCl) followed by resuspension in 1×PCR buffer supplemented with 1.5 mM $MgCl_2$, 200 mM dNTPs, 2 units of Taq polymerase (GIBCO BRL Life Technologies, Gaithersburg, Md.), and 0.44 mg of Taq Antibody (Clontech). One cycle of PCR (5 min at 94° C., 3 min at 50° C., and 5 min at 72° C.) was performed in the presence of the adaptor-oligo(dT) primer and 3-GSP1. The reaction mixture was heated to 95° C. for 2 min to separate the $2^{nd}$ strand cDNA into the liquid phase from the immobilized $1^{st}$ strand cDNA. The liquid phase, contained all the components of the PCR reaction except the immobilized $1^{st}$ strand cDNA, was transferred to a fresh tube and 30 cycles of PCR were performed as described above. Five ml of this reaction were used as template for a second round of PCR using a nested forward primer (3'-GSP2), and an overlapping reverse primer (adaptor primer) for 30 cycles of the following steps: 1 min at 94° C., 2 min at 50° C., and 2 min 30 sec at 72° C.

5' RACE. A separate cDNA library was made for the isolation of the 5' RACE product. mRNA was extracted, and 1st strand cDNA was synthesized as described above. In order to generate a downstream hybridization site for the adaptor oligo(dT) primer for PCR amplification, the 3' end of the 1st strand cDNA was extended with an oligo(dA) tail. After removal of the mRNA., the solid phase cDNA library was resuspended in tailing buffer (0.1M potassium cacodylate, pH 7.2, 2 mM $CoCl_2$, 0.2 mM DTT), 0.2 mM dATP and 10 units of Terminal Deoxynucleotide Transferase (TdT) and incubated at 37° C. for 5 min followed by 5 min at 65° C. in order to inactivate the enzyme. After tailing, PCR was performed (5 min at 95° C., 3 min at 50° C., 5 min at 72° C., for one cycle and then 30 cycles of 1 min at 95° C., 2 min at 50°0 C., 2 min 30 sec at 72° C.) in the same reaction mixture as described above with the following primers: 5'-GSP1, adaptor-oligo $(dT)_{17}$ and adaptor primer. In this case, PCR was carried out in the presence of the magnetic beads. The PCR products were separated from the beads and used as template for the second round of PCR using an overlapping forward primer (adaptor primer) and a nested reverse primer (5'-GSP2).

Genomic PCR. *M. sexta* DNA was amplified by PCR in order to partially sequence the ETH gene. The following protocol was used: 250 ng of *M. sexta* DNA were used as template in 1×Multiplex PCR buffer (6.7 mM $MgCl_2$, 16.6 mM $(NH_4)_2SO_4$, 6.8 mM EDTA, 67 mM Tris, pH 8.8, 10% DMSO, 1.5 mM dXTPs, 5 mM b-mercaptoethanol) to which 10 pmoles of forward and reverse primers, 2 units of Taq polymerase and 0.44 mg of Taq Antibody were added. The PCR reaction was run for 30 cycles of: 1 min at 95° C., 2 min at 50° C., and 2 min 30 sec at 72° C.

ETH PCR Primers. The sequences of the primers used for 3' and 5' RACE PCR were as follows: the adaptor-oligo(dT) primer sequence was 5'-GACTCGAGTCGACATCGA(T)$_{17}$. (SEQ ID NO:5), the adaptor primer sequence was 5'-GACTCGAGTCGACATCG (SEQ ID NO:6), the 3'-GSP1 primer sequence was 5'-TTCGA(TC)CA(AG)GG (N) NO:7), the 3'-GSP2 primer sequence was 5'-GTCAT (ATC)AA(AG)ACIAA(TC)AA(AG)AA (SEQ ID NO:8), the 5'-GSP1 primer sequence was 5'-CGGCTGTGCGTCATCTTCATATAG (SEQ ID NO:9), and the 5'-GSP2 primer sequence was 5'-CCATGGGTAAAGCTTTGGAATATC (SEQ ID NO:10).

The following primers were used for PCR of the ETH gene: the forward primer sequence (bp 27 to 50 of the cDNA) 5'-GTTAGGTGTTCCCGCGTAAACTAG (SEQ ID NO:11), and the reverse primer sequence (bp 463 to 489 of the cDNA) 5'-AATGACTAGAAATTATTTAAGTACAGG (SEQ ID NO:12).

Cloning and Sequencing of MasETH Clones. PCR products were cloned into the pCR™II vector using the TA Cloning Kit according to the manufacturers' instructions (Invitrogen, San Diego, Calif.). Dideoxy double-stranded sequencing of the cloned inserts was performed using the enzyme Sequence 2.0 as described by the manufacturer (United States Biochemical, Cleveland, Ohio.).

RESULTS

Isolation of 3' and 5' RACE PCR Products The amino acid sequence of the MasETH peptide (SNEAISPFDQGMMGYVIKTNKNIPRM-$NH_2$, SEQ ID NO:3, the —NH, indicates that the methionine is amidated) was used to design degenerate gene specific primers (GSPs) in order to generate 3' and 5' RACE (Rapid Amplification of cDNA Ends) products.

Messenger RNA was isolated from *M. sexta* EG by annealing to oligo(dT) residues which were covalently attached to magnetic beads; washing and buffer changes are simplified as the mRNA-beads are pelleted away from the liquid phase by placing the tube against a magnetic stand. This simple, one-tube method allowed the present inventors to isolate message from minute amounts of sample tissue and perform cDNA synthesis reactions with no intervening purification steps and subsequent loss of material. After the second round of 3' RACE PCR, a faint band sized at 0.4 kb was visualized on an agarose gel. Cloning and sequencing of this band showed that it contained the correct DNA sequence as expected from the MasETH peptide sequence (SEQ ID No. 3) at its 5' end. Likewise, a 0.35 kb band was seen after the second round of 5' RACE PCR. The sequence of this cloned product was also determined to be correct as it contained sequence coding for the MasETH peptide at its 3' end.

The length of the transcript was 568 bp with a 345 bp open reading frame coding for 114 amino acids.

EXAMPLE 10

ETH OCTAPEPTIDE

The present example is provided to detail an 8-mer peptide fragment of the ETH protein. Accordingly, peptide preparations that include this octapeptide may be employed within the scope of this invention where the peptide is capable of inducing ecdysis.

The octapeptide identified by the present inventors as providing one of the biologically active peptide of ETH is: Thr-Asn-Lys-Asn-Ile-Pro-Arg-Met (SEQ ID NO.1). This peptide was synthesized using conventional peptide synthesis.

EXAMPLE 11

PRECURSOR ETH cDNA, ETH, ETH-PRP1, and ETH-PRP2

The present example presents the cDNA of precursor ETH, and defines the various peptides identified within the precursor ETH, which include ETH, ETH-PRP1 and ETH-PRP2. These peptide and nucleic acid molecules are particular embodiments of the present invention.

The polypeptide precursor amino acid sequence is provided in Table 3. The precursor is cleaved to provide the following cleavage products: ETH gene-related peptide 2 (ETH-PRP2) extends from amino acid glutamine (Q) at position 20 of Table 3 to valine (V) at position 34 (SEQ ID NO:13), and is further defined as a 15 amino acid peptide. ETH extends from amino acid serine (S) at position 37 to amino acid methionine (M) at position 62 of the sequence in Table 3 (SEQ ID NO: 3), and is further defined as a 26 amino acid peptide. ETH precursor peptide 1 extends from amino acid asparagine (N) at position 66 to amino acid methionine (M) at position 112 of the sequence in Table 2 (SEQ ID NO:14) and is further defined as a 47 amino acid peptide.

Nucleic acid molecules having a nucleotide sequence encoding ETH (SEQ ID NO:18), ETH precursor-related peptide 1 (SEQ ID NO:14), ETH precursor-related peptide 2 (SEQ ID NO:14), ETH precursor cDNA (SEQ ID NO:16) are also identified, and constitute still additional embodiments of the invention (See Table 4).

TABLE 3 - ETH PRECURSOR AMINO ACID SEQUENCE, SEQ ID NO:15

| | | | | | | | | | | | | | | | |
|---|---|---|---|---|---|---|---|---|---|---|---|---|---|---|---|
| M | A | F | R | V | T | K | V | L | T | A | L | C | L | V | 15 |
| C | L | F | L | Q | V | E | S | S | F | I | K | P | N | N | 30 |
| V | P | R | V | G | R | S | N | E | A | I | S | P | F | D | 45 |
| Q | G | M | M | G | Y | V | I | K | T | N | K | N | I | P | 60 |
| R | M | G | R | R | N | Y | D | S | E | N | R | F | D | I | 75 |
| P | K | L | Y | P | W | R | A | E | N | T | E | L | Y | E | 90 |
| D | D | A | Q | P | T | N | G | E | E | I | N | G | F | Y | 105 |
| G | K | Q | R | E | N | M | K | R | | | | | | | 115 |

TABLE 4 - ETH PRECURSOR NUCLEIC ACID SEQUENCE, SEQ ID NO:16

ATG GCC TTT AGG GTA ACT AAG GTA TTA ACG GCG TTG TGC CTA GTA 45
TGT TTA TTT TTG CAA GTG GAA AGT TCA TTT ATT AAG CCA AAT AAT 90
GTA CCG AGG GTA GGC AGA AGC AAT GAA GCT ATT AGC CCA TTC GAT 135
CAA GGA ATG ATG GGG TAT GTG ATT AAA ACT AAT AAA AAT ATA CCA 180
CGC ATG GGA AGA AGA AAC TAT GAT TCG GAA AAT CGT TTC GAT ATT 225
CCA AAG CTT TAC CCA TGG CGT GCC GAA AAT ACA GAA CTA TAT GAA 270

```
GAT GAC GCA CAG CCG ACA AAT GGT GAA GAA ATC AAT GGT TTC TAT   315
GGG AAA CAA CGA GAA AAT ATG AAA CGA TGA                       345
```

EXAMPLE 12

CHEMICAL ANALOGS OF ETH

The present example details chemical analogs of ETH contemplated by the present inventors. These analogs are expected to have improved biological activity and/or enhanced stability. These preparations will provide the active ingredient of the second generation insecticides of the present invention.

ETH as isolated from epitracheal glands of *Manduca sexta* is a 26-amino acid peptide having an amino acid sequence as shown in SEQ ID NO:3 and the peptide is aminated as described in Example 1. The inventors envision modifications to the peptide, or functional equivalents thereof (such as peptide that comprises an amidated octomer of SEQ ID NO:1) that would increase stability and shelf life. For example, the N-terminus may be derivatized with an acetyl group, a pyroglutamate group, or the like, to provide protection from exopeptidase activity; methionine residues may be sensitive to oxidation and may be replaced by isoleucine, norleucine, or the like, while retaining biological activity; and the C-terminus may be derivatized with R groups to form a secondary or tertiary amine. As a replacement for the amide linkage at the C-terminus, it is contemplated that an ester, or thioether linkage may be a functional equivalent.

EXAMPLE 13

ETH AS RESEARCH TOOLS

The discovery of the EG and its product, Mas-ETH, provides a new perspective on the regulation of insect ecdysis and processes associated with this behavior. The EG may serve as a target for ecdysteroids and neuropeptides (for example, eclosion hormone), which could regulate expression and release of Mas-ETH. Thus, the EG provide an excellent model system for basic studies of endocrine processes from molecule to behavior, including regulation of hormone expression, release, and physiological actions.

EXAMPLE 14

ETH FROM SILK MOTHS (*BOMBYX MORI*)

The present example outlines a particular protocol that was used in the isolation of the ETH hormone from silkworm (*bombyx mori*) Inka cells. The present inventors extracted epitracheal glands of pharate pupae of *Bombyx mori* in physiological saline and injected the extract into the hemocoel of pharate larvae, pupae, and adults at various times prior to normal ecdysis. Epitracheal glands (EG) were dissected into a microtissue grinder and kept on dry ice until extraction into Weever's saline. Extracted samples were heated in a 90° C. water bath for 2 to 3 min., cooled on ice, centrifuged at 10,000 g and the supernatant was injected directly into the hemocoel.

The EG extracts triggered ecdysis within minutes of injection at all stages of pharate larvae, pupae and adults.

The peptide employed in this study with ecdysis-triggering activity was purified from an extract of 110 silkmoth pharate pupal EG with reversed-phase liquid chromatography (RPLC) (FIG. 1A). For HPLC fractionation, freshly-dissected EG were homogenized in acidic methanol (MeOH: $H_O$: acetic acid, 90:9:1) and the supernatant was evaporated to dryness. Crude extracts of EG were fractionated with a Microsorb C4 column (wide pore 300 A, 4.6 mm/25 cm), with a linearly increasing gradient of acetonitrile (3 to 53% in 90 min) in constant 0.1% TFA/water using a flow rate of 1 ml/min. ETH was 95% pure after a single fractionation step.

Electrospray mass spectrometry (ES-MS) showed Bom-ETH to have a molecular mass of 2655 Da. Edman microsequencing revealed a polypeptide of 23 amino acids with the sequence shown in SEQ ID NO:2. Automated Edman degradation sequencing was performed with a Porton amino acid sequenator coupled on-line with an HPLC analyzer for identification of PTH-derivatized amino acids. This peptide was named *Bombyx mori* ecdysis triggering hormone, or Bom-ETH.

Synthetic Bom-ETH was prepared according to standard solid phase peptide synthesis methods by Research Genetics, Inc. (Birmingham, AL) to provide a peptide having the amino acid sequence of the 23 mer. Both the amidated and free —COOH terminal forms were prepared. The amidated form co-elutes with the native peptide under a variety of RPLC conditions and is biologically active upon injection into larval insects. The free acid form was observed to not co-elute with the native material, and was found to be biologically inactive when injected at doses much higher than the amidated form.

From these studies, the —COOH terminal amidated form was shown to be the correct structure.

On the basis of RPLC peak integrations, each pharate pupal Inka cell was estimated as containing approximately 5 pmol of Bom-ETH shortly before natural pre-ecdysis. This estimate is based on the assumption that Bom-ETH has a molar extraction coefficient similar to that of Mas-ETH. This assumption is likely to be valid, since aromatic amino acids are the major contributors to UV absorbance, and both Mas-ETH and Bom-ETH contain a single tyrosine and phenylalanine residue, and are devoid of tryptophan.

With 18 Inka cells per *Bombyx mori* animal, it was estimated that there is approximately 100 pmol of Bom-ETH per each of these individual insects. Employing an estimated blood volume of a pharate pupa of 1.0 ml, release of the entire complement of Inka cells is expected to generate as an upper limit, a physiological concentration of 100 nM.

The COOH-terminal amino acid sequence of Bom-ETH, Pro-Arg-Met-$NH_2$, is identical to that of SCPB (Morris, et al. 1982) and may explain the SCPB-like immunoreactivity of the Inka cells. Bom-ETH in the EG is expected to be solely produced by the Inka cells. This is supported by the observations that SCPB-like immunoreactivity has been identified in these studies to be limited to the Inka cells, and because extracts of pharate adult EG, which have only a single Inka cell, show potent ecdysis-triggering activity.

EXAMPLE 15

ECLOSION HORMONE VS ETH BIOACTIVITY

The present inventors have found that ETH, and the material included in pharate pupae, is distinct in several respects from the brain peptide, eclosion hormone. These functional differences relate to onset of pre-ecdysis and ecdysis sensitivity to the respective compositions, and differences in ability to evoke pre-ecdysis behaviors in vitro. The studies demonstrating these functional differences are presented below.

In the present studies, the inventors observed that the tracheal system was required for eclosion hormone to evoke pre-ecdysis and ecdysis behaviors in isolated nerve cord. The tracheal system was not required, however, for ETH to evoke these behaviors.

Other differences between EC and ETH relate to differences in amino acid sequence, relative size, tissue source, and in the onset of sensitivity in insects to ETH versus EH.
Size Eclosion hormone (EH) is a 62-amino acid peptide with internal disulfide bonding. Mas-ETH is a linear, 26 amino acid peptide while Bom-ETH is a linear 23 amino acid peptide. The two hormones have no significant similarity in amino acid sequence.
Source EH is a neuropeptide, synthesized by medial-ventral neurons in the brain. In contrast, ETH is synthesized by glandular tissue, the epitracheal glands. In particular, the Inka cells of the epitracheal gland appear to constitute a rich source of the ETH prior to release of the hormone from these structures at specific development periods.
Responsiveness The present studies indicate that the two hormones act on different target tissues. For example, the early onset of Mas-ETH sensitivity in vivo (1 to 2 days prior to normal ecdysis) contrasts with the relatively narrow period of responsiveness to eclosion hormone near the end of each molt (Thurman, et al., In: *Insect Neurochemistry and Neurophysiology* 1993, pp. 39–51, London: CRC Press). Pharate larvae injected with eclosion hormone 6 to 12 hours prior to normal ecdysis show only pre-ecdysis behavior. Sensitivity for both pre-ecdysis and ecdysis behaviors begins just 6 hours before normal ecdysis. If eclosion hormone is injected at the beginning of this sensitive period, the delay from injection to appearance of both behaviors is about 3 hours. In pharate pupae, responsiveness to eclosion hormone begins at about 8 hours prior to ecdysis, and the delay between injection at this time and onset of behavior is 140 min. Pharate adults show only a 4 hour window of sensitivity. (Id.)
Sensitivity The present inventors' studies on the biological actions of Mas-ETH show that the motor program driving pre-ecdysis and ecdysis in all life stages is already fully competent at developmental stages far earlier than the appearance of sensitivity to the eclosion hormone. The latency to onset of Mas-ETH effects is invariably short, ranging from 2 to 10 min. It follows that the late-emerging sensitivity to eclosion hormone depends on events other than behavioral competence. Sensitivity to eclosion hormone appears to at least be delayed until an onset in the ability of epitracheal glands to release the ecdysis triggering hormone or related peptide/protein as characterized by the present inventors. The disclosure provided here shows that the isolated central nervous system can generate pre-ecdysis and ecdysis motor patterns following Mas-ETH treatment in the absence of the tracheal system. This data contrasts with earlier reports that eclosion hormone (that is, extracts of the adult corpora cardiaca; Weeks, J. C. and Thurman, J. W., *J. Comp. Physiol. A.* 155, 407), does not elicit ecdysis from isolated nerve cords unless the tracheal system and its attachments to the spiracles are intact.

Work by the present inventors demonstrated that corpora cardiaca extracts were ineffective in evoking pre-ecdysis and ecdysis in isolated nerve cords lacking the tracheal system (5 studies). However, these studies also showed that corpora cardiaca extracts were effective in triggering pre-ecdysis and ecdysis bursting patterns in the presence of freshly-dissected pharate pupal EGs. The epitracheal glands (EG) identified by the present inventors are attached to the outer wall of tracheal tubes near each segmental spiracle. The requirement of the tracheal system for eclosion hormone action therefore has been concluded by the present inventors to relate to the presence of the epitracheal glands, rather than the presumed role of the tracheal system in oxygenation of the nervous system. This evidence suggests that eclosion hormone does not act directly on the nervous system, but rather on the Inka cells that reside in the epitracheal gland tissue, thereby causing the release of the novel ecdysis triggering hormone and related peptides disclosed here. The ETH then acts on the nervous system to trigger release of eclosion hormone, and the subsequent ecdysis behavior of the patterned behavior. The regulation of the patterned behavior pre-ecdysis and ecdysis has thus now been redesigned by the identification of the family of ecdysis triggering hormone and its related peptides, disclosed here. Improved insect controlling preparations possessing enhanced insect behavioral regulation activity, are now available employing these ETH and ETH derived preparations.

EXAMPLE 16

ETH-PRECURSOR-RELATED PEPTIDE 1

The present example details studies conducted with ETH-Precursor-related peptide 1 (ETH-PRP1) preparations. This substance was chemically synthesized using standard solid-phase peptide synthesis.

The ETH-PRP1 peptide was dissolved into physiological saline and injected into pharate fifth instar *Manduca sexta* larvae. A dose range of 50 pmol to 5 nmol was tested. Animals responded after a 15–20 min latency by exhibiting preecdysis behavior. However, unlike the results obtained with ETH, ETH-PRP1 did not elicit ecdysis behavior.

When injected into insect larvae as described above, ETH-PRP1 causes cardioacceleration. Thus, one function of ETH-PRP1 may be to facilitate the dispersal of co-released ETH into the circulation so as to promote the ecdysis process.

EXAMPLE 17

ETH-Precursor Related Peptide 2

This peptide was derived from the precursor molecule sequence for ETH. It is contemplated that it has an amino acid sequence as defined in SEQ ID NO:13, and a nucleic acid sequence as defined in SEQ ID NO:17.

The present example details the discovery of ETH-precursor-related peptide 2 (ETH-PRP2). This peptide is deduced from the nucleotide sequence of the ETH precursor. The —COOH terminal sequence, -Val-Pro-Arg-val-amide (SEQ ID NO:28) is homologous to that of Mas-ETH, and also shows similarity to a cardioacceleratory peptide, CAP2B (Huesmann, et al., 1995). The probable N-terminal amino acid, Gln is indicated by the fact that many insect peptides having —COOH terminal -Arg-Phe-amide sequences have N-terminal Gln, which spontaneously cyclizes to form pyroglutamic acid.

ETH-PRP2 enhances the physiological actions of Mas-ETH by increasing its ecdysis triggering activity and furthermore acts as a cardioaccelerator to provide more efficient distribution of the co-released Mas-ETH into the circulatory system.

EXAMPLE 18

INSECTICIDAL PREPARATIONS/ VIRAL DELIVERY STRATEGIES

The present example details several insecticidal preparations that employ both sense and antisense nucleic acid sequences for the ETH, ETH-precursor, ETH-PRP1 and ETH-PRP2 peptides/proteins herein disclosed.

The antisense sequence for the ETH-PRP2 is provided at SEQ ID NO:24. The sense sequences for these various peptides/proteins are as previously described herein.

VIRAL CONSTRUCTS—SENSE NUCLEIC ACID SEQUENCES

The synthetic encoding ETH, or alternatively,its cDNA precursor, will be incorporated into a suitable viral vector, such as a baculovirus. In one particular embodiment, the virus may be AcNPV; *Autographa californica* nuclear polyhedrosis virus. However, many other viral carriers may be used with equal efficacy.

The coding region for ETH, Precursor ETH, ETH-PRP1, ETH-PRP2, or a combination construct of these sequences, will be flanked at the 3' end with by an appropriate signal sequence. By way of example, such an appropriate 3' flanking signal sequence may comprise the adipokinetic hormone signal described in Bradfield and Keeley (1989). The 5' end will be flanked by an appropriate stop codon (e.g., TAA). The expression of the ETH or related hormone sequences will be under the control of appropriate promoters, such as "p10", "polyhedrin", or "basic protein".

Constructs will be ligated into suitable vector elements, such as pACUW21 for a single promoter construct or pACU51 for multiple promoter constructs. Detailed descriptions of various types of viruses, constructs, and vectors are found in O'Reily et al, 91992), Baculovirus expression vectors. A laboratory manual. New York, W. H. Freeman Co.), which reference is specially incorporated herein by reference for this purpose.

Constructed viral vectors carrying the ETH or related protein/peptide encoding nucleic acid sequence will then be used as the delivery system for use as insecticides. The virus will be formulated according to standard field application protocols and sprayed onto crop plants. The occluded virus (OV) enters the insect via the oral route and is solubilized in the alkaline midgut, releasing embedded virions. The virions enter the midgut cells and subsequently enter the hemocoel as budded virus (BV) and is then transported to other tissues via the circulatory system and along the tracheal network via epidermal cells.

The infection process results in cessation of insect feeding within 5-7 days. Expression of insect hormones such as ETH at the inappropriate time will result in more rapid cessation of feeding and development.

VIRAL CONSTRUCTS—ANTISENSE STRATEGIES

The antisense sequence for *Manduca sexta* full length cDNA ETH precursor is provided at SEQ ID NO:20. The antisense sequence of the *Manduca sexta* cDNA ETH precursor, is provided at SEQ ID NO:21. The antisense sequence of the *Manduca sexta* ETH is provided at SEQ ID NO: 22. The antisense sequence for the *Manduca sexta* ETH-PRP1 is provided at SEQ ID NO:23. Antisense sequence for ETH PRP2 is provided at SEQ ID NO. 24. Viral constructs containing one or a combination of these antisense sequences, or receptors for these hormones alone or in combination with the antisense sequence for eclosion hormone, or its receptor, will be prepared using standard viral construct techniques. The strategy used will be essentially the same as that outlined for sense sequence containing constructs.

These viral constructs would then be applied to crop plants, and thus deliver anti-hormone sequences to pests, and present successful molting of the insect. Such would result insignificant reduction in insect numbers, and hence associated crop loss.

EXAMPLE 19

USE OF ETH IN INCREASING YIELD OF SILKWORM COCOONS

ETH may be used in a method of increasing the yield of silkworm cocoons. U.S. Pat. No. 3,941,879, incorporated by reference herein in particular for methods of rearing and feeding silkworm larvae and use of juvenile hormone, relates to a method for increasing yield of silkworm cocoons employing juvenile and molting hormones. When juvenile hormone is administered to silkworm larvae in an early stage of their final instar and molting hormone is administered to them in a later stage of the same instar, the inventors of U.S. Pat. No. 3,941,879 found that the yield of cocoons per unit amount of feedstuff, namely, feed efficiency, was remarkable increased. The molting hormone used in their invention includes sterones and materials obtainable from plants.

The method of the present invention would comprise administering to silkworm larvae, orally or through the body surface by means of spraying or dipping, at an early stage of their final instar, an insect juvenile hormonal factor which prevents silkworm larvae from metamorphosis, and ETH at a later stage of their final instar. Application of ETH will provide a means of synchronizing the ecdysis of a population of silkworms, thus enhancing the percentage yield of unblemished silk cocoons.

EXAMPLE 20

FIELD USE OF ETH AND RELATED PROTEINS

The present example defines particular commercial applications of the ETH and ETH precursor related peptides 1 and 2.

A preparation of ETH that provides a dose of between about 20 pmol to about 2 nmol of the ETH to an insect in a given area or the biologically active peptide thereof, is expected to provide the induction of ecdysis and/or premature eclosion insecticidal action described here at Examples 3 and 4, most preferably, the nucleic acid molecule encoding the ETH will be prepared in a viral vector, and the viral vector then applied, for example, as a spray, to a population of insects present in a sprayed field.

Expressed as Kg/hectare, it is expected that preparations containing the ETH, ETH-PRP1, ETH-PRP2, or a combination thereof, at a dose range of from 0.5-200 Kg/hectare, will be sufficient to essentially disrupt the normal growth and maturation process of the insects. The amount to be applied is further described as an insect population controlling effective amount.

Any variety of carriers may be used for those compositions containing ETH, ETH-PRP1, ETH-PRP2, or a combination of them. Because activity is enhanced with improved contact and penetration of those agents, DMSO and other like carriers may be used to facilitate uptake. Accordingly, the ETH, ETH-PRP1, ETH-PRP2 or mixture thereof, is to be dissolved in about 30% aqueous DMSO and applied as a spray to a population of insects. The ETH, ETH-PRP1 and ETH-PRP2 of the present preparations, in some embodiments, are substantially free from associated insect polypeptides.

EXAMPLE 21

FUNCTIONAL STUDY OF SYNTHETIC ETH: CARBOXY-TERMINUS

The present example demonstrates that replacement of the amide moiety on the carboxy-terminal methionine results in loss of biological activity.

The amidated and acid form of the 26 mer of SEQ ID NO:3 was prepared using a solid state synthesizer. This procedure is the same as that described at example 7. The amidated and acid forms of ETH used in the present study were synthesized by Research Genetics Corporation using these standard protocols (5 mg. each of the amidated-ETH and the acid-ETH).

Pharate fourth instar *Manduca sexta* larvae (liquid-filled head capsule stage) were injected with synthetic ETH and an isomer thereof, wherein the C-terminal methionine had a free carboxyl group. As little as 1 pmol of ETH-amide caused preecdysis followed by ecdysis, whereas 40 pmol of ETH-acid caused no discernible behavioral response.

From these results, the inventors conclude that the C-terminal end of ETH is essential to the ecdysis triggering hormone activity of the protein.

EXAMPLE 21

ETH RECEPTOR CHARACTERIZATION AND ISOLATION

The nucleic acid sequence for the ETH precursor (SEQ.ID NO.16) will be used to isolate the ETH receptor according to the present invention. The cDNA encoding ETH precursor will be used as a probe (e.g., radiolabelled with $^{125}I$, $^{3}H$, biotinylated or dewaterized in a substance) for use in characterizing and cloning its receptor. Production of the ETH receptor will then be pursued, and will permit its use in biological screening to direct synthesis of small organic chemicals that would mime the action of the peptide and serve as chemical insecticides, acting to promote or inhibit ecdysis at the appropriate time in insect development.

EXAMPLE 23

ECLOSION HORMONE RECEPTOR AND ECDYSIS TRIGGERING HORMONE RECEPTOR CHARACTERIZATION AND ISOLATION

The present example details a method by which the receptor for eclosion hormone is to be identified and cloned.

The strategy for identifying the EH receptor and ETH receptor is basically that described in Reagan, J. D., (1994). The first step will be to obtain tissue that is responsive to EH (Inka cells) or ETH (central nervous system). Extract mRNA from this tissue and reverse transcribe to obtain cDNA for construction of a cDNA library.

cDNA is then to be ligated into a suitable expression vector (pcDNA3 or pcDM8) for expression cloning using COS-7 cells. The cDNA library is then to be used to transform COS cells, which express the receptor and insert it into the plasma membrane. COS cells are then screened with labelled ETH or EH for receptor binding to clones expressing the appropriate receptor. Detection is by autoradiography. Clones showing binding are selected and purified, then grown to obtain the cDNA encoding the receptor. The receptor DNA sequence will then be obtained by standard sequencing approaches.

EXAMPLE 24

SCREENING ASSAY FOR ETH RECEPTOR BINDING COMPOUNDS

The present example describes a method for selecting agents that bind the ETH receptor. These compounds are expected to be topically active for inducing insect ecdysis. As such, these compounds are particularly suitable for formulation into insecticidal preparations as sprays and for water treatments. Identification of small organic chemicals which mime or antagonize the action of ETH would have enhanced topical activity, be economical to manufacture, and could be optimized for stability under field conditions.

The receptor for ETH or EH will be established in a cell line that can conveniently be grown up to permit large-scale screening of small organic hormone-mimetics or anti-hormones. The ETH or EH receptor as isolated according to Example 24 would be incorporated into a suitable plasmid (ex.: pACUW21), which then is used to transform a clonal cell line [examples of clonal cell line: Sf21, *Spodoptera frugiperda* embryonic cell line or human embryonic kidney (HEK) cell line].

Test groups of small organic compounds will then be screened for ability to inhibit the binding of the appropriate radioligand (ETH or ETH). Such a compound would serve as an anti-hormone, and ideally would be useful as a contact insecticide.

Alternative screens, depending on the nature of the receptor once it is characterized If the receptor is coupled to a GTP-binding protein, the selected clonal cell line will be transformed with the receptor (ETH or EH) plus a suitable G-protein and reporter gene, such as luciferase. Binding of an efficacious ligand to the receptor would lead to a chemiluminescence response. Such a compound would serve as a hormone-mimetic.

In the event that the receptor has kinase activity (e.g., tyrosine kinase), the assay could involve measurement of phosphorylation products after exposure to candidate compounds, or inhibition of a normal phosphorylation response after exposure t the nature ligands (EH or ETH).

EXAMPLE 25

ENHANCED GROWTH AND SYNCHRONIZATION OF DEVELOPMENT WITH ETH AND GENE RELATED PEPTIDES/PROTEINS

The present example relates to the use of the various peptides of the invention, either alone or together with other agents, to synchronize the development of a population of insects, crustaceans, silkworms, or other ETH-sensitive animals. In this manner, increased yields of commercially important products may be realized.

Silk Production

As a growth regulator, ETH can be administered during the last larval instar in conjunction with juvenile hormones and ecdysis-like steroids to produce supernumerary molts yielding larger cocoons and increased silk yields Enhanced yield will also be expected from synchronization of insect development.

Lobster/Crab Production

A number of commercially important aquatic animals, including for example lobsters and crab (blue crab), shed their outer skin at some point during development. The present invention also proposes a method for inducing this behavior in these animals by treating with the ETH or derivatives thereof described in the present disclosure. Maturation of animals may be manipulated in this fashion to provide for example, population of freshly emerged blue crab enriched in a given pool of treated animals.

All of the compositions and methods disclosed and claimed herein can be made and executed without undue experimentation in light of the present disclosure.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Atherton, E. and Sheppard, R. C. (1989), "Solid Phase Peptide Synthesis, a Practical Approach", IRL Press at Oxford University Press.

Bell, et al., *Ann. Entomol. Soc. Am.* 69, 365–376 (1976)

Bradfield, J. Y. and Keeley, L. L. (1989), "Adipokinetic hormone gene sequence from Manduca sexta", *J. Biol. Chem.*, 264 (22): 12791–3

Copenhaver, P. F., and J. W. Truman, *J. Insect. Physiol.* 28, 695 (1982)

Curtis, A. T., et al. *J. Insect Physiol.* 30, 597 (1984)

Ewer, J., V. J. De Vente, J. W. Truman, *J. Neurosci.* 14, 7704–12 (1994)

Fields, G. B. and Noble, R. L. (1990) "Solid phase peptide synthesis utilizing 9-fluorenylmethoxycarbonyl amino acids", Int. *J. Peptide Protein Res.*, 35, 161–214

Hewes, R. S., and J. W. Truman, *J. Comp. Physiol.* [a] 168, 697 (1991)

Huesmann, G. R., Cheung, C. C., Loi, P. K., Lee, T. D. and Tublitz, N. (1995), "Amino acid sequence of CAP2B, an insect cardioacceleratory peptide from the tobacco hawkmoth *Manduca sexta*", *FEBS Lett.* 371: 311–314 Jan, L. Y., and Y. N. Jan, *Proc. Natl. Acad. Sci. USA* 79, 2700; 1982

Keilin, D., *Parasitology,* 36, 1, (1944)

Kyte & Doolittle (1982) *J. Mol. Biol.* 157:105–132

Marti, et al., *Febs Letters,* 219(2): 415–418 (1987)

Masinovsky, B., et al., *J. Comp. Neurol.* 273, 500; 1988

Maeda, S., et al. *Virology* 184, 777–80 (1991).

Miles, C. I., and J. C. Weeks, *J Comp Physiol* [A] 168, 179 (1991)

Morris, H. R., et al., *Nature* 300, 643 (1982)

O'Reilly, D. R., Miller, L. K. and Luckow, V. A. (1992), "Baculovirus expression vectors", *A laboratory manual,* New York. W. H. Freeman and Co.

Reagan, J. D. (1994), "expression cloning of an insect diuretic hormone receptor. A member of the calcitonin/secretin receptor family", *J. Biol. Chem.* 269(1): 9–12.

Reynolds, S. E., et al., J. Exp. Biol. 78, 77 (1979)

Sambrook et al. (1989). Molecular cloning: A laboratory manual.

Cold Spring Harbor Laboratory, Cold Spring Harbor, N.Y.

Stewart, L. M., et al. *Nature* 352, 85–8 (1991).

Tomalski, M. D. & Miller, L. K. *Nature* 352, 82–5 (1991).

Trimmer, B. A., et al., *J. of Comp. Neurology.* 266:16–26 (1987) Truman, J. W., and J. C. Weeks, in Model Neural Networks and *Behavior* A. I. Selverston, Eds. (Plenum Press, New York, 1985) pp. 381–399

Truman J. W., and J. C. Weeks, in *Neural Control of Rhythmic Movements* A. Roberts, B. L. Roberts, Eds. (Cambridge University Press, Cambridge, 1983), vol. 37, pp. 223–41

Truman, J. W., *J. Exp. Biol.* 74, 151 (1978)

Truman, J. W., *Prog. Brain Res.* 92, 361 (1992)

Truman, J. W., et al., in: *Insect Neurochemistry and Neurophysiology* 1993 A. B. Borkovec, M. J. Loeb, Eds. (CRC Press, London, 1994) pp. 39–51

Truman, J. W. et al., *J. Exp. Biol.* 88, 327 (1980)

Truman, J. W., et al., *J. Exp. Biol.* 89D 327 (1980)

Troetschler, et al., (1985), *J. Econ. Entomol.* 78, 1521–1523 (1985)

Weeks, J. C., and J. W. Truman, *J. Comp. Physiol* A 155, 407 (1984)

Weeks, J. C., and J. W. Truman, *J. Comp. Physiol.* A 155, 423 (1984)

Zitnan, D., Ph. D dissertation, Slovak Academy of Sciences, 1989

Zitnan, D., et al., *Dev. Biol.* 156, 117 (1993)

U.S. Pat. No. 5,082,828—Schooley, et al. (1992)

U.S. Pat. No. 3,941,879—Okauchi, et al. (1976)

It is understood that the invention disclosed herein is not necessarily confined to the particular elements illustrated and therefore may be practiced in the absence of any element riot specifically disclosed herein or in the presence of additional elements.

What is claimed is:

1. A composition comprising a substantially purified ecdysis triggering hormone, or a fragment of ecdysis triggering hormone that has the ecdysis triggering hormone activity, said ecdysis triggering hormone comprising SEQ ID NO:1.

2. The composition of claim 1, wherein the ecdysis triggering hormone is further defined as comprising a sequence as set forth from about amino acid Ser at position 37 to amino acid Met at position 62 of SEQ ID NO:3.

3. The composition of claim 1, wherein the ecdysis triggering hormone of claim 1 further defined as having a molecular mass of between about 2000 to about 3500 Da, as determined by liquid secondary ion mass spectrometry.

4. The composition of claim 3, wherein the ecdysis triggering hormone further defined as having a molecular weight of between about 2500 to about 3500 Da, as determined by liquid secondary ion mass spectrometry.

5. The composition of claim 3, wherein the ecdysis triggering hormone is further defined as having a molecular weight of about 2600 to about 3000 Da, as determined by liquid secondary ion mass spectrometry.

6. The composition of claim 5, wherein the ecdysis triggering hormone is further defined as a *Manduca sexta* ecdysis triggering hormone having a molecular weight of about 2940 as determined by liquid secondary ion mass spectrometry.

7. A preparation for use in the control of insects comprising as an active ingredient an ecdysis triggering amount of the ecdysis triggering hormone of claim 1, in a carrier.

8. The preparation of claim 7 wherein the carrier is further defined as capable of penetrating an insect cuticle.

9. The preparation of claim 8 wherein the carrier is DMSO.

10. A composition comprising a substantially pure ecdysis triggering hormone comprising an amino acid sequence as set forth in SEQ ID NO:2.

11. An ecdysis triggering hormone comprising SEQ ID NO:1, substantially free from associated insect polypeptide prepared by a process comprising:

extracting insects to provide an insect extract;

obtaining ecdysis-active fractions from said insect extract; and concentrating the ecdysis-triggering active fractions to obtain a composition comprising a substantially purified ecdysis triggering hormone, having a molecular weight of about 2000 Da to about 3000 Da as determined by liquid secondary ion mass spectrometry.

12. A method for preparing a substantially purified ecdysis triggering hormone:

extracting insects to provide an insect extract;

obtaining ecdysis-triggering active fractions from said insect extract; and concentrating the ecdysis-active fractions to obtain a composition comprising a substantially purified ecdysis triggering hormone, having a molecular weight of about 2000 Da to about 3000 Da as determined by liquid secondary ion mass spectrometry, wherein said ecdysis triggering hormone comprises SEQ ID NO:1.

13. The method of claim 12 wherein the insects are lepidopteran insects.

14. A method for preparing an ecdysis triggering hormone comprising:

obtaining epitracheal glands of lepidopteran insects to provide a lepidopteran epitracheal gland preparation;

extracting the lepidopteran epitracheal gland preparation in saline to provide an extracted lepidopteran epitracheal gland extract;

heating the extract to provide a heat-treated insect extract;

cooling the heat-treated extract to provide a cooled insect extract;

centrifuging the cooled insect extract; and collecting the supernatant, said supernatant comprising the ecdysis triggering hormone having a molecular weight of between about 2000 to about 3500 Da as determined by liquid secondary ion mass spectrometry.

15. The method of claim 14 wherein the ecdysis triggering hormone is further defined as having a molecular weight of about 2300 to about 3000 Da.

16. An ecdysis triggering hormone precursor related peptide-1 having a molecular weight of about 5,500 to about 5,800 Da as determined by liquid secondary ion mass spectrometry, and comprising an amino acid sequence of amino acid Asn at position 66 through amino acid Met at position 112 of SEQ ID NO:14.

17. The ecdysis triggering hormone precursor related peptide-1 of claim 16 further defined as comprising SEQ ID:14.

18. A substantially purified ecdysis triggering hormone precursor related peptide-2, said peptide having an amino acid sequence as defined by amino acid Gln at position 20 through amino acid Val at position 34 of SEQ ID NO:13.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:1:

Thr  Asn  Lys  Asn  Ile  Pro  Arg  Met
    1                      5

( 2 ) INFORMATION FOR SEQ ID NO:2:

( i ) SEQUENCE CHARACTERISTICS:
        ( A ) LENGTH: 23 amino acids
        ( B ) TYPE: amino acid
        ( D ) TOPOLOGY: linear ( x i ) SEQUENCE DESCRIPTION: SEQ ID NO:2:

```
Ser Asn Glu Ala Phe Asp Glu Asp Val Met Gly Tyr Val Ile Lys Ser
1               5                   10                  15
Asn Lys Asn Ile Pro Arg Met
            20
```

( 2 ) INFORMATION FOR SEQ ID NO:3:

( i ) SEQUENCE CHARACTERISTICS:
        ( A ) LENGTH: 26 amino acids
        ( B ) TYPE: amino acid
        ( D ) TOPOLOGY: linear ( x i ) SEQUENCE DESCRIPTION: SEQ ID NO:3:

```
Ser Asn Glu Ala Ile Ser Pro Phe Asp Gln Gly Met Met Gly Tyr Val
1               5                   10                  15
Ile Lys Thr Asn Lys Asn Ile Pro Arg Met
            20                  25
```

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
ACNAAYAARA AYATHCCNMG NATG                                24
```

( 2 ) INFORMATION FOR SEQ ID NO:5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
GACTCGAGTC GACATCGATT TTTTTTTTT TTTTT                     35
```

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
GACTCGAGTC GACATCG                                        17
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TTCGAYCARG GNATGATGGG        20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 12
        ( D ) OTHER INFORMATION: /note= "base #12 is an inosine"

( x i ) SEQUENCE DESCRIPTION: SEQ ID NO:8:

GTCATHAARA CNAAYAARAA        20

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CGGCTGTGCG TCATCTTCAT ATAG        24

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CCATGGGTAA AGCTTTGGAA TATC        24

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GTTAGGTGTT CCCGCGTAAA CTAG        24

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

AATGACTAGA AATTATTTAA GTACAGG        27

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:13:

Gln Val Glu Ser Ser Phe Ile Lys Pro Asn Asn Val Pro Arg Val
1               5                   10                  15

( 2 ) INFORMATION FOR SEQ ID NO:14:

( i ) SEQUENCE CHARACTERISTICS:
    ( A ) LENGTH: 47 amino acids
    ( B ) TYPE: amino acid
    ( D ) TOPOLOGY: linear ( x i ) SEQUENCE DESCRIPTION: SEQ ID NO:14:

Asn Tyr Asp Ser Glu Asn Arg Phe Asp Ile Pro Lys Leu Tyr Pro Trp
1               5                   10                  15

Arg Ala Glu Asn Thr Glu Leu Tyr Glu Asp Asp Ala Gln Pro Thr Asn
                20                  25                  30

Gly Glu Glu Ile Asn Gly Phe Tyr Gly Lys Gln Arg Glu Asn Met
                35                  40                  45

( 2 ) INFORMATION FOR SEQ ID NO:15:

( i ) SEQUENCE CHARACTERISTICS:
    ( A ) LENGTH: 114 amino acids
    ( B ) TYPE: amino acid
    ( D ) TOPOLOGY: linear ( x i ) SEQUENCE DESCRIPTION: SEQ ID NO:15:

Met Ala Phe Arg Val Thr Lys Val Leu Thr Ala Leu Cys Leu Val Cys
1               5                   10                  15

Leu Phe Leu Gln Val Glu Ser Ser Phe Ile Lys Pro Asn Asn Val Pro
                20                  25                  30

Arg Val Gly Arg Ser Asn Glu Ala Ile Ser Pro Phe Asp Gln Gly Met
                35                  40                  45

Met Gly Tyr Val Ile Lys Thr Asn Lys Asn Ile Pro Arg Met Gly Arg
                50                  55                  60

Arg Asn Tyr Asp Ser Glu Asn Arg Phe Asp Ile Pro Lys Leu Tyr Pro
65                  70                  75                  80

Trp Arg Ala Glu Asn Thr Glu Leu Tyr Glu Asp Asp Ala Gln Pro Thr
                85                  90                  95

Asn Gly Glu Glu Ile Asn Gly Phe Tyr Gly Lys Gln Arg Glu Asn Met
                100                 105                 110

Lys Arg ( 2 ) INFORMATION FOR SEQ ID NO:16:

( i ) SEQUENCE CHARACTERISTICS:
    ( A ) LENGTH: 345 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

| | | | | | | |
|---|---|---|---|---|---|---|
| ATGGCCTTTA | GGGTAACTAA | GGTATTAACG | GCGTTGTGCC | TAGTATGTTT | ATTTTTGCAA | 60 |
| GTGGAAAGTT | CATTTATTAA | GCCAAATAAT | GTACCGAGGG | TAGGCAGAAG | CAATGAAGCT | 120 |
| ATTAGCCCAT | TCGATCAAGG | AATGATGGGG | TATGTGATTA | AAACTAATAA | AAATATACCA | 180 |
| CGCATGGGAA | GAAGAAACTA | TGATTCGGAA | AATCGTTTCG | ATATTCCAAA | GCTTTACCCA | 240 |
| TGGCGTGCCG | AAAATACAGA | ACTATATGAA | GATGACGCAC | AGCCGACAAA | TGGTGAAGAA | 300 |
| ATCAATGGTT | TCTATGGGAA | ACAACGAGAA | AATATGAAAC | GATGA | | 345 |

( 2 ) INFORMATION FOR SEQ ID NO:17:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
CAAGTGGAAA  GTTCATTTAT  TAAGCCAAAT  AATGTACCGA  GGGTA                   45
```

( 2 ) INFORMATION FOR SEQ ID NO:18:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
AGCAATGAAG  CTATTAGCCC  ATTCGATCAA  GGAATGATGG  GGTATGTGAT  TAAAACTAAT   60

AAAAATATAC  CACGCATG                                                    78
```

( 2 ) INFORMATION FOR SEQ ID NO:19:

( i ) SEQUENCE CHARACTERISTICS:
        ( A ) LENGTH: 141 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
AACTATGATT  CGGAAAATCG  TTTCGATATT  CCAAAGCTTT  ACCCATGGCG  TGCCGAAAAT   60

ACAGAACTAT  ATGAAGATGA  CGCACAGCCG  ACAAATGGTG  AAGAAATCAA  TGGTTTCTAT  120

GGGAAACAAC  GAGAAAATAT  G                                              141
```

( 2 ) INFORMATION FOR SEQ ID NO:20:

( i ) SEQUENCE CHARACTERISTICS:
        ( A ) LENGTH: 568 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
GAGACATCGT  TTGTTCGTTT  AAACGTGTTA  GGTGTTCCCG  CGTAAACTAG  TTTTGTTCTT   60

AAAATGGCCT  TTAGGGTAAC  TAAGGTATTA  ACGGCGTTGT  GCCTAGTATG  TTTATTTTTG  120

CAAGTGGAAA  GTTCATTTAT  TAAGCCAAAT  AATGTACCGA  GGGTAGGCAG  AAGCAATGAA  180

GCTATTAGCC  CATTCGATCA  AGGAATGATG  GGTATGTGA   TTAAAACTAA  TAAAAATATA  240

CCACGCATGG  GAAGAAGAAA  CTATGATTCG  GAAAATCGTT  TCGATATTCC  AAAGCTTTAC  300

CCATGGCGTG  CCGAAAATAC  AGAACTATAT  GAAGATGACG  CACAGCCGAC  AAATGGTGAA  360

GAAATCAATG  GTTTCTATGG  GAAACAACGA  GAAAATATGA  ACGATGATT   ATATTCTGGA  420

ACGATGAATA  TTAGTTTACG  GCAGTCAAAT  CAAATGTTTT  TCCCTGTACT  TAAATAATTT  480

CTAGTCATTT  ATTTTATAAA  ATAAACAGAT  GCATGCATTA  AAAAAAAAA   AAAAAAAAA   540

AAAAAAAAA   AAAAAAAAA   AAAAAAA                                         568
```

( 2 ) INFORMATION FOR SEQ ID NO:21:

( i ) SEQUENCE CHARACTERISTICS:
    ( A ) LENGTH: 518 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

| | | | | | |
|---|---|---|---|---|---|
| ATGCATGCAT | CTGTTTATTT | TATAAAATAA | ATGACTAGAA | ATTATTTAAG | TACAGGGAAA | 60 |
| AACATTTGAT | TTGACTGCCG | TAAACTAATA | TTCATCGTTC | CAGAATATAA | TCATCGTTTC | 120 |
| ATATTTTCTC | GTTGTTTCCC | ATAGAAACCA | TTGATTTCTT | CACCATTTGT | CGGCTGTGCG | 180 |
| TCATCTTCAT | ATAGTTCTGT | ATTTTCGGCA | CGCCATGGGT | AAAGCTTGG | AATATCGAAA | 240 |
| CGATTTTCCG | AATCATAGTT | TCTTCTTCCC | ATGCGTGGTA | TATTTTATT | AGTTTAATC | 300 |
| ACATACCCCA | TCATTCCTTG | ATCGAATGGG | CTAATAGCTT | CATTGCTTCT | GCCTACCCTC | 360 |
| GGTACATTAT | TTGGCTTAAT | AAATGAACTT | TCCACTTGCA | AAAATAAACA | TACTAGGCAC | 420 |
| AACGCCGTTA | ATACCTTAGT | TACCCTAAAG | GCCATTTTAA | GAACAAAACT | AGTTTACGCG | 480 |
| GGAACACCTA | ACACGTTTAA | ACGAACAAAC | GATGTCTC | | | 518 |

( 2 ) INFORMATION FOR SEQ ID NO:22:

( i ) SEQUENCE CHARACTERISTICS:
    ( A ) LENGTH: 81 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

| | | | | | |
|---|---|---|---|---|---|
| TCCCATGCGT | GGTATATTTT | TATTAGTTTT | AATCACATAC | CCCATCATTC | CTTGATCGAA | 60 |
| TGGGCTAATA | GCTTCATTGC | T | | | | 81 |

( 2 ) INFORMATION FOR SEQ ID NO:23:

( i ) SEQUENCE CHARACTERISTICS:
    ( A ) LENGTH: 141 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

| | | | | | |
|---|---|---|---|---|---|
| CATATTTTCT | CGTTGTTTCC | CATAGAAACC | ATTGATTTCT | TCACCATTTG | TCGGCTGTGC | 60 |
| GTCATCTTCA | TATAGTTCTG | TATTTTCGGC | ACGCCATGGG | TAAAGCTTTG | GAATATCGAA | 120 |
| ACGATTTTCC | GAATCATAGT | T | | | | 141 |

( 2 ) INFORMATION FOR SEQ ID NO:24:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

| | | | | |
|---|---|---|---|---|
| GCCTACCCTC | GGTACATTAT | TTGGCTTAAT | AAATGAACTT | TCCACTTG | 48 |

( 2 ) INFORMATION FOR SEQ ID NO:25:

( i ) SEQUENCE CHARACTERISTICS:
    ( A ) LENGTH: 143 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

ATGTACAAGC TCACAGTCTT CCTGATGTTC ATCGCTTTCG TCATAATCGC TGAAGCCTCA　　　60

AACGAAGCAA TATCGCCATT CGACAAGGCA TGATGGGATA CGTTATTAAA ACAAACAAAA　　　120

ACATTCCAAG AATGGGCTAA TAG　　　143

( 2 ) INFORMATION FOR SEQ ID NO:26:

( i ) SEQUENCE CHARACTERISTICS:
　　　　( A ) LENGTH: 4 amino acids
　　　　( B ) TYPE: amino acid
　　　　( D ) TOPOLOGY: linear ( x i ) SEQUENCE DESCRIPTION: SEQ ID NO:26:

Ser Asn Glu Ala
　　1

( 2 ) INFORMATION FOR SEQ ID NO:27:

( i ) SEQUENCE CHARACTERISTICS:
　　　　( A ) LENGTH: 6 amino acids
　　　　( B ) TYPE: amino acid
　　　　( D ) TOPOLOGY: linear ( x i ) SEQUENCE DESCRIPTION: SEQ ID NO:27:

Met Gly Tyr Val Ile Lys
　　1　　　　　　　　　5

( 2 ) INFORMATION FOR SEQ ID NO:28:

( i ) SEQUENCE CHARACTERISTICS:
　　　　( A ) LENGTH: 4 amino acids
　　　　( B ) TYPE: amino acid
　　　　( D ) TOPOLOGY: linear ( x i ) SEQUENCE DESCRIPTION: SEQ ID NO:28:

Val Pro Arg Val
　　1

( 2 ) INFORMATION FOR SEQ ID NO:29:

( i ) SEQUENCE CHARACTERISTICS:
　　　　( A ) LENGTH: 4 amino acids
　　　　( B ) TYPE: amino acid
　　　　( D ) TOPOLOGY: linear ( x i ) SEQUENCE DESCRIPTION: SEQ ID NO:29:

Phe Met Arg Phe
　　1